US010036032B2

(12) United States Patent
Juarez et al.

(10) Patent No.: US 10,036,032 B2
(45) Date of Patent: Jul. 31, 2018

(54) METHODS AND COMPOSITIONS FOR WATERMELON FIRMNESS

(71) Applicant: Seminis Vegetable Seeds, Inc., St. Louis, MO (US)

(72) Inventors: Benito Juarez, Woodland, CA (US); Joseph J. King, Davis, CA (US); Eleni Bachlava, Vallejo, CA (US); Adam M. Wentzell, Winters, CA (US); Jeffrey M. Mills, Woodland, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 275 days.

(21) Appl. No.: 14/743,682

(22) Filed: Jun. 18, 2015

(65) Prior Publication Data

US 2015/0376635 A1 Dec. 31, 2015

Related U.S. Application Data

(62) Division of application No. 13/600,612, filed on Aug. 31, 2012.

(60) Provisional application No. 61/529,667, filed on Aug. 31, 2011.

(51) Int. Cl.
*A01H 5/08* (2018.01)
*A01H 1/04* (2006.01)
*C12Q 1/68* (2018.01)
*C12N 15/82* (2006.01)
*C12Q 1/6895* (2018.01)

(52) U.S. Cl.
CPC ........... *C12N 15/8261* (2013.01); *A01H 5/08* (2013.01); *C12Q 1/6895* (2013.01); *C12Q 2600/13* (2013.01); *C12Q 2600/156* (2013.01); *C12Q 2600/158* (2013.01)

(58) Field of Classification Search
CPC ............................... A01H 5/08; C12Q 1/6827
See application file for complete search history.

(56) References Cited

U.S. PATENT DOCUMENTS

| | | | |
|---|---|---|---|
| 5,866,764 A | 2/1999 | Gabor et al. | |
| 6,096,944 A | 8/2000 | Vierling et al. | |
| 6,207,367 B1 | 3/2001 | Helentjaris et al. | |
| 6,399,855 B1 | 6/2002 | Beavis | |
| 6,414,226 B1 | 7/2002 | Hoogstraten | |
| 6,639,132 B1 | 10/2003 | Duvick et al. | |
| 6,670,530 B2 | 12/2003 | Eby et al. | |
| 2003/0172412 A1 | 9/2003 | Zhang et al. | |
| 2005/0015827 A1 | 1/2005 | Podlich et al. | |
| 2005/0204780 A1 | 9/2005 | Moridaira et al. | |
| 2005/0216545 A1 | 9/2005 | Aldrich et al. | |
| 2005/0218305 A1 | 10/2005 | Tsukamoto et al. | |
| 2006/0005284 A1 | 1/2006 | Tolla et al. | |
| 2009/0031438 A1 | 1/2009 | Kennard et al. | |
| 2010/0306883 A1 | 12/2010 | Tolla et al. | |
| 2013/0055466 A1 | 2/2013 | Juarez et al. | |
| 2015/0101072 A1 | 4/2015 | Lanini | |

FOREIGN PATENT DOCUMENTS

WO   WO 03/051103 A2   6/2003
WO   WO 03/096798 A1   11/2003

OTHER PUBLICATIONS

Sandlin (Genetic Mapping in Citrullus lanatus, Thesis, University of Georgia, Dec. 2010.*
Sandlin (Genetic Mapping in Citrullus lanatus, Thesis, University of Georgia, Dec. 2010 (Year: 2010).*
Abstracts of the ASHS Southern Region 50th Annual Meeting, *HortScience*, 25(8):848-865 (1990).
Alkridge et al., Spring 2009 and 2010 Commercial Fruit and Vegetable Variety Trails, Regional Bulletin 22, Alabama's Agricultural Experiment Station, Auburn University, pp. 1-32 (2011).
Andrus et al., "Production of Seedless Watermelons," *Agricultural Research Service*, USDA Technical Bulletin No. 1425, pp. 1-15 (1971).
Articles about US Seedless Watermelons, *US Seedless Press*, pp. 1-3 (1999) <http://www.usseedless.com/press/htm>.
Bang et al., "Deficit irrigation impact on lycopene, soluble solids, firmness and yield of diploid and triploid watermelon in three distinct environments," *Journal of Horticultural Science*, 79(6):885-890 (2004).
Bang, "Environmental and Genetic Strategies to Improve Carotenoids and Quality in Watermelon," Ph.D. Thesis, Texas A&M University, pp. 1-127 (2005).
Buttrose et al., "Some Effects of Light Intensity, Daylength and Temperature on Growth of Fruiting and Non-fruiting Watermelon (*Citrullus lanatus*)," *Ann. Bot.*, 42:599-608 (1978).
Cartaxo et al., "Controlled Atmosphere Storage Suppresses Microbial Growth on Fresh-Cut Watermelon," *Proc. Fla. State Hort. Soc.*, 110:252-257 (1997).
Chen et al., "Gene Transfer via Pollen-Tube Pathway for Anti-Fusarium Wilt in Watermelon," *Biochemistry and Molecular Biology International*, 46(6):1201-1209 (1998).
Crall et al., "Florida 'Icebox' Cultivars as a Factor in Watermelon Production in Florida and Other Producing States," *Soil and Crop Sci. Soc. Fla. Proc.*, 45:132-134 (1986).
Crall et al., "SSDL: A High-quality Icebox Watermelon Breeding Line Resistant to Fusarium Wilt and Anthracnose," *HortScience*, 29(6):707-708 (1994).
Crall, "'Charlee' Watermelon," *HortScience*, 25(7):812-813 (1990).
Crall, "Fifty Years of Watermelon Breeding at ARC Leesburg," *Proc. Fla. State Hort. Soc.*, 94:156-158 (1981).
Eigsti, "Improvement of Watermelon with Polyploids," *Cucurbit Genetics Cooperative Report CGC2-15*, 2(article 15):25-26 (1979).
EMBL Online Database Accession No. CS490596, "Sequence 29 from Patent WO2007003397," pp. 1 (2007).
(Continued)

*Primary Examiner* — Lee A Visone
(74) *Attorney, Agent, or Firm* — Alissa Eagle; Arnold & Porter Kaye Scholer LLP

(57) ABSTRACT

The invention provides for unique watermelon plants with an ultra-firm flesh phenotype and their progeny. Such plants may comprise an introgressed QTL associated with an ultra-firm flesh phenotype. In certain aspects, compositions, including distinct polymorphic molecular markers, and methods for producing, breeding, identifying, selecting, and the like of plants or germplasm with an ultra-firm flesh phenotype are provided.

15 Claims, 4 Drawing Sheets

(56) References Cited

OTHER PUBLICATIONS

Extended European Search Report dated Jun. 15, 2012, as received in European Patent Application No. 12151233.9.
Extended European Search Report dated Mar. 25, 2015, as received in European Patent Application No. 12827082.4.
Extended European Search Report dated Sep. 14, 2009, as received in European Patent Application No. 05764293.6.
Fonseca et al., "Shock and Vibration Forces Influence the Quality of Fresh-Cut Watermelon," *Proc. Fla. State Hort. Soc.*, 112:147-152 (1999).
Gamborg, "Plant Tissue Culture, Biotechnology, Milestones.," *In Vitro. Cell. Dev. Biol. Plant*, 38:84-92 (2002).
Geneseq Online Database Accession No. ABH42851, "Oligonucleotide SEQ ID No. 242828 for detecting SNP TSC0059263" (2002).
Gillies et al., "Cooling Method Influences the Postharvest Quality of Broccoli," *HortScience*, 30(2):313-315 (1995).
Gilreath et al., "Evaluation of Icebox Watermelon Cultivars in West Central and Southwest Florida," *Proc. Fla. State Hort. Soc.*, 99:331-334 (1986).
Griffith, "The Significance of Pneumococcal Types," *Journ. of Hyg.*, XXVII(2):114-159 (1928).
GRIN Online Database Accession No. Grif 15895, "Sugar Baby," pp. 1-2 (2003).
GRIN Online Database Accession No. PI 296341, "Tsamma," pp. 1-2 (1964).
GRIN Online Database Accession No. PI 635683, "Sweet Siberian," pp. 1-2 (1963).
Guner et al., "Gene List for Watermelon," *Cucurbit Genetics Cooperative Report*, 26:76-92 (2003).
Gunter et al., "Elongated Seedless Watermelon Cultivar Trials for Southwestern Indiana, 2003," Southwest Purdue Agricultural Program, Purdue University, pp. 1-2 (2003).
Gunter et al., "Evaluation of Non-Harvested Watermelon Pollenizers for Flowering Characteristics and *Fusarium oxysporum* fsp. *niveum* Susceptibility," Southwest Purdue Agricultural Program, Purdue University, pp. 1-10 (2006).
Gunter et al., "Personal Sized Seedless Watermelon Cultivar Trials for Southwestern Indiana, 2004," Southwest Purdue Agricultural Program, Purdue University, pp. 1-2 (2004).
Gunter et al., "Personal Sized Seedless Watermelon Cultivar Trials for Southwestern Indiana, 2005," Southwest Purdue Agricultural Program, Purdue University, pp. 1-2 (2005).
Gunter et al., "Seeded Watermelon Cultivar Trials for Southwestern Indiana, 2003," Southwest Purdue Agricultural Program, Purdue University, pp. 1-2 (2003).
Gunter et al., "Seeded Watermelon Cultivar Trials for Southwestern Indiana, 2004," Southwest Purdue Agricultural Program, Purdue University, pp. 1-2 (2004).
Gunter et al., "Seeded Watermelon Cultivar Trials for Southwestern Indiana, 2005," Southwest Purdue Agricultural Program, Purdue University, pp. 1-2 (2005).
Gunter et al., "Seeded Watermelon Cultivar Trials for Southwestern Indiana, 2001," Southwest Purdue Agricultural Program, Purdue University, pp. 1-2 (2001).
Gunter et al., "Seedless Watermelon Cultivar Trials for Southwestern Indiana, 2007," Department of Horticulture Science, North Carolina State University, pp. 1-8 (2007).
Gunter et al., "Seedless Watermelon Cultivar Trials for Southwestern Indiana, 2001," Southwest Purdue Agricultural Program, Purdue University, pp. 1-2 (2001).
Gunter et al., "Seedless Watermelon Cultivar Trials for Southwestern Indiana, 2003," Southwest Purdue Agricultural Program, Purdue University, pp. 1-2 (2003).
Gunter et al., "Seedless Watermelon Cultivar Trials for Southwestern Indiana, 2004," Southwest Purdue Agricultural Program, Purdue University, pp. 1-3 (2004).
Gunter et al., "Seedless Watermelon Cultivar Trials for Southwestern Indiana, 2006," Southwest Purdue Agricultural Program, Purdue University, pp. 1-4 (2006).
Gunter et al., "Seedless Watermelon Cultivar Trials for Southwestern Indiana, 2005," Southwest Purdue Agricultural Program, Purdue University, pp. 1-3 (2005).
Gusmini et al., "Rind Thickness of Watermelon Cultivars for Use in Pickle Production," *HortTechnology*, 14(4):540-545 (2004).
Gusmini, "Watermelon (*Citrullus lanatus*) Breeding Handbook," North Carolina State University, Raleigh, NC, pp. 1-90 (2003).
Hashizume et al., "Construction of a linkage map and QTL analysis of horticultural traits for watermelon [*Citrullus lanatus* (Thunb.) Matsum & Nakai] using RAPD, RFLP and ISSR markers," *Theor. Appl. Genet.*, 106:779-785 (2003).
Hawkins et al., "Linkage Mapping in a Watermelon Population Segregating for Fusarium Wilt Resistance," *J. Amer. Soc. Hort. Sci.*, 126(3):344-350 (2001).
Henderson et al., "Interaction of Flesh Color Genes in Watermelon," *Journal of Heredity*, 89(1):50-53 (1998).
Henderson, "Inheritance of Orange Flesh Color in Watermelon," *Cucurbit Genetics Cooperative Report CGC12-26*, 12(article 26):59-63 (1989).
Holmes et al., "Cucurbitaceae 2006 Proceedings," *Universal Printing & Publishing*, Raleigh, NC, pp. 1-602 (2006).
Hybrid Watermelon, *Jeffreys Seed Company Online: Vegetable Seed Catalog*, pp. 1-4, n.d., Web, Mar. 30, 2004 <http://www.jeffreys-seed.com/vegetable_seed/watermelon_02.html>.
International Preliminary Report on Patentability dated Mar. 10, 2009, as received in International Application No. PCT/US2005/023902.
International Preliminary Report on Patentability dated Mar. 4, 2014, as received in International Application No. PCT/US2012/053476.
International Search Report dated Apr. 9, 2008, as received in International Application No. PCT/US2005/023902.
International Search Report dated Jan. 25, 2013, as received in International Application No. PCT/US2012/053476.
Jaskani et al., "Comparative study on vegetative, reproductive and qualitative traits of seven diploid and tetraploid watermelon lines," *Euphytica*, 145:259-268 (2005).
Kang et al., "Inheritance of Lobed Leaf, Plant Shape, and Sugar Content in Watermelon (*Citrullus lanatus* (Thunb.) Matsum. et. Nakai)," *Korean J. Breed.*, 32(4):315-316 (2000).
Kano, "Effects of summer day-time temperature on sugar content in several portions of watermelon fruit (*Citrullus lanatus*)," *J. Hort. Sci. Biotechnol.*, 79(1):142-145 (2004).
Karakurt et al., "Cell wall-degrading enzymes and pectin solubility and depolymerization in immature and ripe watermelon (*Citrullus ianatus*) fruit in response to exogenous ethylene," *Physiologia Plantarum*, 116:398-405 (2002).
Karchi et al., "'Alena' Watermelon," *HortScience*, 16(4):573 (1981).
Karchi et al., "Alena" Watermelon: A Quality Cultivar for Export and Local Markets, *Hassadeh*, 61(8):1284-1285 (1981).
Karchi et al., "The Importance of Cultural Practices in Materializing Yield Potential in a Tetraploid Watermelon Cultivar," *Cucurbit Genetics Cooperative Report CGC6-30*, 6(article 30):59-61 (1983).
Kemble, "Watermelon Grader's Guide ANR-681," *Alabama Cooperative Extension System*, pp. 1-4 (2001).
Kumar, Inheritance of Fruit Yield and other Horticulturally important Traits in Watermelon [*Citrullus lanatus* (Thunb.) Matsum. & Nakai]., Ph.D. Thesis, North Carolina State University, pp. 1-128 (2009).
Lam et al., "Grafted Seedless Watermelon Trial in Southwest Indiana (2006)," Southwest Purdue Agricultural Program, Purdue University, pp. 1-4 (2006).
Leskovar et al., "Deficit Irrigation Influences Yield and Lycopene Content of Diploid and Triploid Watermelon," *Acta Hort.*, 628:147-151 (2003).
Leskovar et al., "Lycopene, carbohydrates, ascorbic acid and yield components of diploid and triploid watermelon cultivars are affected by deficit irrigation," *Journal of Horticultural Science & Biotechnology*, 79(1):75-81 (2004).
Levi et al., "A Genetic Linkage Map for Watermelon Based on Randomly Amplified Polymorphic DNA Markers," *J. Amer. Soc. Hort. Sci.*, 126(6):730-737 (2001).

(56) References Cited

OTHER PUBLICATIONS

Levi et al., "An Extended Genetic Linkage Map for Watermelon Based on a Testcross and a $BC_2F_2$ Population," *American Journal of Plant Sciences*, 2:93-110 (2011).

Levi et al., "Genetic diversity among watermelon (*Citrullus lanatus* and *Citrullus colocynthis*) accessions," *Genetic Resources and Crop Evolution*, 48:559-566 (2001).

Levi et al., "Low Genetic Diversity Indicates the Need to Broaden the Genetic Base of Cultivated Watermelon," *HortScience*, 36(6):1096-1101 (2001).

Lou, "Inheritance of Fruit Characteristics in Watermelon [*Citrullus lanatus* (Thunb.) Matsum. & Nakai]," Ph.D. Thesis, North Carolina State University, pp. 1-134 (2009).

Mao et al., "Incidence of water-soaking and phospholipid catabolism in ripe watermelon (*Citrullus lanatus*) fruit: induction by ethylene and prophylactic effects of 1-methylcyclopropene," *Postharvest Biology and Technology*, 33:1-9 (2004).

Martyn et al., "Resistance to Races 0, 1, and 2 of Fusarium Wilt of Watermelon in *Citrullus* sp. PI-296341-FR," *HortScience*, 26(4):429-432 (1991).

Maynard et al., "Triploid Watermelon Cultigen Evaluation Spring 2003," Gulf Coast Research and Education Center, GCREC Research Report BRA-2003, pp. 1-5 (2003).

Mitchell et al., "Fruit Yield, Quality Parameters, and Powdery Mildew (*Sphaerotheca fuliginea*) Susceptibility of Speciality Melon (*Cucumis melo* L.) Cultivars Grown in a Passively Ventilated Greenhouse," *Cucurbitaceae 2006*, pp. 483-491 (2006).

Morales et al., "Seeded Watermelon Cultivar Trials for Southwestern Indiana, 2000," Department of Horticulture, Purdue University, pp. 1-2 (2000).

Morales et al., "Seedless Watermelon Cultivar Trials for Southwestern Indiana, 2000," Department of Horticulture, Purdue University, pp. 1-2 (2000).

Nerson et al., "Harvesting Watermelons Before Ripening Impairs Their Quality," *Hassadeh*, 62:606-607 (1981).

Netzer et al., "PI 296341, a Source of Resistance in Watermelon to Race 2 of *Fusarium oxysporum* f. sp. *niveum*," *Plant Disease*, 73(6):518 (1989).

Nip et al., "Physical, Chemical and Organoleptic Attributes of 'Charleston Gray' Watermelons at Different Stages of Maturity," *Proc. Amer. Soc. Hort. Sci.*, 93:547-551 (1968).

North Carolina Watermelon Association Newsletter, Oct. 10, 2003—Fall Edition, pp. 1-5 (2003).

Orange Fleshed Seedless Watermelon Varieties, *US Seedless Press*, pp. 1-2, n.d., Web, Oct. 1, 2014 <http://www.usseedless.com/orange_varieties.htm>.

Perkins-Veazie et al., "Flesh quality and lycopene stability of fresh-cut watermelon," *Postharvest Biology and Technology*, 31:159-166 (2004).

Perkins-Veazie et al., "Shelf Life of Minimally Processed Watermelon," *HortScience*, 33(4):605 (1998).

Picha, "Storage temperature influences watermelon quality," *Louisiana Agriculture*, 31(2):4-5 (1998).

Plant Variety Protection Certificate No. 8500103 for 'Charlee,' issued Oct. 31, 1986 in the name of Florida Agricultural Experiment Station.

Plant Variety Protection Certificate No. 8600105 for 'Minilee,' issued Jan. 30, 1987 in the name of Florida Agricultural Experiment Station.

PlantFiles: Watermelon *Citrullus lanatus* 'Alena,' *Dave's Garden*, pp. 1-2, n.d., Web, Dec. 23, 2009 <http://davesgarden.com/guides/pf/go/92716/index.html>.

Porter, "Inheritance of Certain Fruit and Seed Characters in Watermelons," *Hilgardia*, 10(12):489-509 (1937).

Risse et al., "Sensitivity of Watermelons to Ethylene During Storage," *HortScience*, 17(6):946-948 (1982).

Risse et al., "Storage Characteristics of Small Watermelon Cultivars," *J. Amer. Soc. Hort. Sci.*, 115(3):440-443 (1990).

Saha et al., "Evaluation of Seedless Watermelon Varieties for Production in Southwest Indiana—2010," *Midwest Vegetable Trial Report for 2010*, pp. 1-7 (2010).

Saha et al., "Evaluation of Triploid Personal-size Watermelon Varieties for Production in Southwest Indiana—2010," *Midwest Vegetable Trial Report for 2010*, pp. 1-3 (2010).

Saha et al., "Kentucky Triploid Watermelon Variety Trial—2014," *Midwest Vegetable Trial Report for 2014*, pp. 1-6 (2014).

Saha et al., "Midwest Personal-Size Triploid Watermelon Variety Trial in Southwest Indiana—2011," *Midwest Vegetable Trial Report for 2011*, pp. 1-3 (2011).

Saha et al., "Midwest Triploid Watermelon Variety Trial in Southwest Indiana—2011," *Midwest Vegetable Trial Report for 2011*, pp. 1-4 (2011).

Saha et al., "Southwest Indiana Triploid Watermelon Variety Trial—2013," *Midwest Vegetable Trial Report for 2013*, pp. 1-10 (2013).

Saha et al., "Watermelon and Muskmelon Variety Trials 2010," *Midwest Vegetable Trial Report for 2010*, pp. 1-27 (2010).

Saha, "Evaluation of Diploid Watermelon Varieties for Production in Southwest Indiana—2010," *Midwest Vegetable Trial Report for 2010*, pp. 1-2 (2010).

Saha et al., "Southwest Indiana Triploid Watermelon Variety Trial—2012," *Midwest Vegetable Trial Report for 2012*, pp. 1-8 (2012).

Sandlin, "Genetic Mapping in *Citrullus lanatus*," Master of Science Thesis, University of Georgia, pp. 1-84 (2010).

Schultheis et al., "2006 Cucurbit Cultivar Evaluations," *Horticultural Research Series No. 165*, North Carolina State University, pp. 1-69 (2006).

Showalter, "Deformation and Breakage Properties of Watermelon Flesh," Watermelon Flesh Studies, *Proc. Fla. State Hort. Soc.*, 81:235-239 (1968).

Slater et al., "Plant Biotechnology: the genetic manipulation of plants 39," Chapter 2: Plant tissue culture, Chapter 2, *Oxford University Press*, Oxford, pp. 37-53 (2003).

Smith, "Embryo Culture of a Tomato Species Hybrid," *Proc. Am. Soc. Hort. Sci.*, 44:413-416 (1944).

Srivastava et al., "Tissue culture and plant regeneration of watermelon (*Citrullus vulgaris* Schrad. cv. Melitopolski), *Plant Cells Reports*, 8:300-302 (1989).

Strang et al., "Triploid Mini-Watermelon Variety Trial," Department of Horticulture, University of Kentucky, pp. 1-4 (2004).

Toivonen et al., "Differences in Chlorophyll Loss at 13° C. for Two Broccoli (*Brassica oleracea* L.) Cultivars Associated with Antioxidant Enzyme Activities," *J. Agric. Food Chem.*, 46:20-24 (1998).

United States Standards for Grades of Watermelons, Effective Mar. 23, 2006, Fresh Products Branch, Fruit and Vegetable Programs, Agricultural Marketing Research, U.S. Department of Agriculture, pp. 1-10 (2004).

Watermelon Millionaire Seedless F1, *Harris Seeds*, pp. 1-2, n.d., Web, Jul. 11, 2015 <https://www.harrisseeds.com/storefront/p-406-watermelon-millionaire-seedless-fl.aspx>.

Wehner et al., "Breeding and Seed Production," In: D.N. Maynard (ed.), Watermelons: Characteristics, production, and marketing, *ASHS Horticulture Crop Production Series*, Chapter 3, pp. 27-73 (2001).

Wehner et al., "Qualitative Genes for Use in Development of Elite Watermelon Cultivars," *Cucurbit Genetics Cooperative Report*, 27:24-24 (2004).

Wehner et al., "Vegetable Cultivar Descriptions for North America List 27 2013," Vegetable Cultivar List, *HortScience*, 48(2):245, 276-286 (2013).

Wehner, "Watermelon," Department of Horticultural Science, North Carolina State University, Index of Cucurbit Wehner Articles, Book 16, pp. 368-405 (2007) <http://cuke.hort.ncsu.edu/cucurbit/wehner/articles/book16.pdf>.

Yamasaki et al., "Mineral Concentrations and Cytokinin Activity in the Xylem Exudate of Grafted Watermelons as Affected by Rootstocks and Crop Load," *J. Japan. Soc. Hort. Sci.*, 62(4):817-826 (1994).

Yoo et al., "Variation of Carotenoid, Sugar, and Ascorbic Acid Concentrations in Watermelon Genotypes and Genetic Analysis," *Hort. Environ. Biotechnol.*, 53(6):552-560 (2012).

(56) References Cited

OTHER PUBLICATIONS

Zhumei et al., "Selection and cultivation of the high quality early ripe variety Nongfong No. 1 B," Pingzhong Shuanyu (*Chinese J. Selection and Cultivation of variety*), 3:11-13 (2004).
Articles about US Seedless Watermelons, *US Seedless Press*, pp. 1-3 (1999).
Crall et al., "Florida 'Icebox' Cultivars as a Factor in Watermelon Production in Florida and Other Producing States," *Soil and Crop Sci. Soc. Fla. Proc.*, 4:132-134 (1986).
Crall, "'Charlee' Watermelon," *HortScience*, 25(7):812-13 (1990).
Database Accession No. ABH42851, "Oligonucleotide SEQ ID No. 242828 for detecting SNP TSC0059263" (2002).
Database Accession No. CS490596, "Sequence 29 from Patent WO2007003397" (2007).
Database Accession No. Grif 15895, "Sugar Baby" (2003).
Database Accession No. PI 296341, "Tsamma" (1964).
Database Accession No. PI 635683, "Sweet Siberian" (1963).
Hybrid Watermelon, *Jeffreys Seed Company*, pp. 1-4 (2002).
International Preliminary Report on Patentability dated Mar. 19, 2009, as received in International Application No. PCT/US2005/023902.
Karakurt et al., "Cell wall-degrading enzymes and pectin solubility and depolymerization in immature and ripe watermelon (*Citrullus lanatus*) fruit in response to exogenous ethylene," *Physiologia Plantarum*, 116:398-405 (2002).
Karchi et al., "The Importance of Cultural Practices in Materializing Yield Potential in a Tetraploid Watermelon Cultivar," *Cucurbit Genetics Cooperative Report*, 6:59-61 (article 30) (1983).

Leskovar et al., "Deficit Irrigation Influences Yield and Lycopene Content of Diploid and Triploid Watermelon," *Acta Hort.*, 628:147-151 (2002).
Leskovar et al., "Lycopene, carboyhdrates, ascorbic acid and yield components of diploid and triploid watermelon cultivars are affected by deficit irrigation," *Journal of Horticultural Science & Biotechnology*, 79(1):75-81 (2004).
Li et al., "Selection and cultivation of the high quality early ripe variety Nongfong No. 1 B," *Chinese J. Selection and Cultivation of Variety*, 3:11-13 (2004).
Maynard et al., "Triploid Watermelon Cultigen Evaluation," Gulf Coast Research and Education Center, GCREC Research Report BRA-2003, pp. 1-5 (2003).
Orange Fleshed Seedless Watermelon Varieties, *US Seedless Press*, pp. 1-2, Web, Oct. 1, 2014 <http://www.usseedless.com/orange_varieties.htm>, retrieved from internet.
Perkins-Veazie et al., "Shelf Life of Minimally Processed Watermelon," *HortScience*, 33(4):605 (1988).
Sandlin, "Genetic Mapping in *Citrullus lanatus*," Thesis, University of Georgia, pp. 1-84 (2010).
Showalter, "Deformation and Breakage Properties of Watermelon Flesh," *Proc. Fla. State Hort. Soc.*, 81:235-239 (1968).
Slater et al., "Chapter 2: Plant tissue culture," Plant Biotechnology: the genetic manipulation of plants, *Oxford University Press*, pp. 37-53 (2003).
Strang et al., "Triploid Mini-Watermelon Variety Trial" (Department of Horticulture, University of Kentucky, Lexington, KY) (2004).
Wehner et al., "Breeding and Seed Production," Watermelons, Characteristics, production, and Marketing, Maynard (ed.), ASHS Horticulture Crop Production Series, Chapter 3, pp. 27-73 (2001).

* cited by examiner

SEQUENCE LISTING

<160> NUMBER OF SEQ ID NOS: 18

<210> SEQ ID NO 1
<211> LENGTH: 120
<212> TYPE: DNA
<213> ORGANISM: Citrullus lanatus
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: allele
<222> LOCATION: (61)..(61)
<223> OTHER INFORMATION: r = g or a or deletion

<400> SEQUENCE: 1
gacaactgca agagaantttt ttcaacatga acattcttc agcaaggaat gttatcgagc     60
ragcgtttgg gttgctaaag cagcagtggg ctattcttag tgaaacataa ttctatccaa    120

<210> SEQ ID NO 2

```
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: w = a or t/u

<400> SEQUENCE: 2
ttgaaagtta ttcgtttact gaatgatgag gcgattggca tatcaaaagt ctcctttatt      60
wgacgaggct aagagttgtg gatatgatct ggaagttgtc tctttctctc atattcgtta     120
t                                                                    121

<210> SEQ ID NO 3
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a

<400> SEQUENCE: 3
ggtggaacta agctcgacaa caatgagcat caacctaccg agcgagaagg cactattgcg      60
rttagcaaca tggaaaagta gtcctgatct tcgttctcgt gtagactatg tcttaggact     120
t                                                                    121

<210> SEQ ID NO 4
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a
<220> FEATURE:
<221> NAME/KEY: misc_feature
<222> LOCATION: (77)..(77)
<223> OTHER INFORMATION: n is a, c, g, or t

<400> SEQUENCE: 4
ggactccagc cagaacatag acatccccca ccccatctg aaaaactaat attgtcccca       60
rtgtgagaaa agaaaanaag agcatgggac aaatgagaag ggaaacaaag aacttccctg     120
a                                                                    121

<210> SEQ ID NO 5
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: m = a or c

<400> SEQUENCE: 5
tcaacaataa ccctagagaa gaccttaaca aacacttgaa ggattttcac atctgaggac      60
mtttccattc tctttgaagg atggacaaat gattggttgt actatcaacc tcctggatcg     120
a                                                                    121

<210> SEQ ID NO 6
<211> LENGTH: 105
<212> TYPE: DNA
<213> ORGANISM: Citrullus lanatus
<220> FEATURE:
```

<221> NAME/KEY: allele
<222> LOCATION: (45)..(45)
<223> OTHER INFORMATION: m = a or c or deletion

<400> SEQUENCE: 6
tgcaggtatc cttatgatct gaaatatcat caagattaca cttamtcgct tgaataatca    60
gaaatttcaa agtgtttatt tacctgtaat cttcaaaaag aagca    105

<210> SEQ ID NO 7
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c or deletion

<400> SEQUENCE: 7
aggataaaca aattcacata cacttttccc aaatacattt aaaaggaaaa ttggagaggg    60
ycaaataagt caagaggcta agctgtaatg aatataacag ctttgttcaa gttaaaccaa    120
t    121

<210> SEQ ID NO 8
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c or deletion

<400> SEQUENCE: 8
acaaaattct ttccaaaaat gtaaaattct caattatgga agttggcgc cgcgatgcta    60 ytggctagag ccgcggtgct gtgcgtcatg caaacctacc ctcggcgctg tgccgcagcg    120

<210> SEQ ID NO 9
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: m = a or c or deletion

<400> SEQUENCE: 9
gaaatttagg ccacccacat gccttcttcg agtccttcag cattgggggt tatctttgta    60
mtcgagttac ccacatgcct tgtccgagtc cttcaacatt gggaaccatt tctatatctc    120
g    121

<210> SEQ ID NO 10
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 10
cttctcggaa atacttcatc tctatggaca tcaccttcct tgaggataaa cccttctttc    60
ycgttagtcc tcgtcaggga gagagtagta gtgaagagac taactgttca tcaccttcaa    120

```
<210> SEQ ID NO 11
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: r = g or a
<220> FEATURE:
<221> NAME/KEY: misc_feature
<222> LOCATION: (108)..(108)
<223> OTHER INFORMATION: n is a, c, g, or t

<400> SEQUENCE: 11
ggtcacagat tcaatctcta aagttgtatg ccaccaaact tagaacctgc aattactacg      60
ratttgacat ccatatacca caaatgaatc tacacgtttg ttgttttnaa tgaactaaaa     120
a                                                                    121

<210> SEQ ID NO 12
<211> LENGTH: 120
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 12
atattcgagt tggccaaata ggtaacttat tattttcttg agtttgttaa catgataata      60
ytactcaacg aaatcctatg atagctacac atttgagaat gcataaacaa actcgtattg     120

<210> SEQ ID NO 13
<211> LENGTH: 99
<212> TYPE: DNA
<213> ORGANISM: Citrullus lanatus
<220> FEATURE:
<221> NAME/KEY: allele
<222> LOCATION: (61)..(61)
<223> OTHER INFORMATION: k = g or t/u

<400> SEQUENCE: 13
aaaattttat gtacaggctg ttacagttcg tcctttatct gctgtcagct ccctcgtacg      60
ktttgcagag gagccccaga tgtttgccat tgaattact                            99

<210> SEQ ID NO 14
<211> LENGTH: 120
<212> TYPE: DNA
<213> ORGANISM: Citrullus lanatus
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: allele
<222> LOCATION: (61)..(61)
<223> OTHER INFORMATION: w = a or t/u
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
```

-continued

<400> SEQUENCE: 14
gtttggaact gttatatccc cntaaactgc tcaatgttat ctcagagtga gcttctacca    60
wtaaagctcc ttgttctggt nccaaaaaac acttccacct tccnattttt nggtctctct   120

<210> SEQ ID NO 15
<211> LENGTH: 120
<212> TYPE: DNA
<213> ORGANISM: Citrullus lanatus
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: allele
<222> LOCATION: (61)..(61)
<223> OTHER INFORMATION: y = t/u or c
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t

<400> SEQUENCE: 15
caattgctgc agatgtaact gaaagaacaa tcaangttct aggatggcat cattttgagt    60
ytagtttcct aataaagtgt tcatctgtgt tttngatgtg ctaaatcagt ggaggcnttt   120

<210> SEQ ID NO 16
<211> LENGTH: 121
<212> TYPE: DNA
<213> ORGANISM: Citrullus lanatus
<220> FEATURE:
<221> NAME/KEY: allele
<222> LOCATION: (61)..(61)
<223> OTHER INFORMATION: y = t/u or c

<400> SEQUENCE: 16
tgacggcggt tgctgcattg ctcatggctg tatggttcat gtctacgatt ggatgctcga    60
ygaacaccct ccgatcaatc tcgattatca gcgagtcaac gatgttgggt ggatcgatgc   120
t                                                                  121

<210> SEQ ID NO 17
<211> LENGTH: 121
<212> TYPE: DNA
<213> ORGANISM: Citrullus lanatus
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: allele
<222> LOCATION: (61)..(61)
<223> OTHER INFORMATION: r = g or a

<400> SEQUENCE: 17
acttaattga atctaataga tgaagttcaa ttacgcaagt acaaaaantt actagttaat    60
rtgtcataca cgcaagtcaa agatctttat gcatggtgcc tccaatttgt tatcagagac   120
c                                                                  121

<210> SEQ ID NO 18
<211> LENGTH: 121
<212> TYPE: DNA
<213> ORGANISM: Citrullus lanatus

```
<220> FEATURE:
<221> NAME/KEY: allele
<222> LOCATION: (61)..(61)
<223> OTHER INFORMATION: y = t/u or c

<400> SEQUENCE: 18
gtatcttttg tgtccgtatt agcttgcgac ctcttcgagt ggttatagtt aggttgtacg      60
ytttgatgtt tttctatgtt ggtatgagtg gcttggggat tcttttcgga gcattcatgt     120
t                                                                     121
```

METHODS AND COMPOSITIONS FOR WATERMELON FIRMNESS

CROSS-REFERENCE TO RELATED APPLICATIONS

This application is a divisional application of U.S. application Ser. No. 13/600,612, filed Aug. 31, 2012, which claims the benefit of U.S. Provisional Patent Application No. 61/529,667, filed Aug. 31, 2011, which is incorporated herein by reference in its entirety.

INCORPORATION OF SEQUENCE LISTING

A sequence listing contained in the file named "P34231US02SeqListing.txt" which is 7,312 bytes (measured in MS-Windows) and comprising 18 nucleotide sequences, created on Jun. 17, 2015, is electronically filed herewith and is incorporated herein by reference in its entirety.

BACKGROUND OF THE INVENTION

Watermelon [*Citrullus lanatus*], is an important commercial member of the Cucurbitaceae family. The fruits display a wide range of coloring on the outside rind. Color in the edible tissue varies from different shades of red to orange to yellow to white. Additional variation in the marketplace can be found with both seeded and seedless types. Unlike the flesh coloring—which is caused by varying genetic loci—the distinction between seeded and seedless varieties is usually caused by varying the ploidy levels.

It is known that there is a correlation between ploidy level and flesh firmness. (U.S. patent application Ser. No. 12/856,286, which is incorporated herein in its entirety). Diploid lines typically have the lowest flesh firmness levels. For reasons that are unclear, the process of changing a diploid line to a tetraploid line correlates with firmer fruit flesh, and thus, tetraploid lines usually have firmer fruit flesh than diploids. Triploids, being a cross between a tetraploid and a diploid, have an intermediate level of fruit firmness.

There is increasing consumer demand in the fresh produce business for products that combine quality and convenience. Examples of products that meet these criteria included bagged mini-carrots and leafy crops, like lettuce and spinach. Similarly, there is a demand for mature cut fruits, like watermelon, melon, mango, pineapple, papaya, and kiwi. In watermelon fruits, one consumer quality criteria is sweetness. Sweetness can be estimated by measuring the total soluble solids, or Brix, using a refractometer. Indeed, fruit quality standards for Brix levels have been established (United States Standards for Grades of Watermelon, U.S. Department of Agriculture (1978)). According to these standards, edible parts of the fruit having not less than 8 Brix are deemed to be "Good," while edible parts of the fruit having not less than 10 Brix are deemed to be "Very Good."

A growing segment of watermelon retail sales are offering to the consumer fruits that are cut and displayed with the rinds attached, or fruits with the rinds removed and where the edible flesh is cut into smaller pieces. The industry term for these products is "minimally processed." In 1998, Perkins-Veazie et al. [(1998) Hortscience 33:605] estimated that 10% of the retail watermelon market was minimally processed.

In addition to offering convenience to the consumer, one advantage of cut fruit displays is that the consumer can visually inspect the quality of the fruit, and in particular, judge whether the fruit is mature and ready to consume. Often, immature fruits will not be uniform in pigmentation, and overripe fruit will display signs of decay.

The disadvantage to the produce retailer in presenting minimally processed watermelon products is that cut fruits have a short shelf life. Studies suggest that minimally processed products have a short shelf life of about 2 to 3 days maximum (ibidem; Wehner et al. In: Watermelons: Characteristics, Production and Marketing. Maynard, editor. ASHS Press, Alexandria Va. 2001).

Watermelon fruits currently available typically undergo rapid quality deterioration after being cut. Deterioration is manifested as juice leakage; in some varieties, the flesh of a fresh cut watermelon fruit becomes unattractive to the consumer quickly. Cutting the fruit also causes decay, which is observed as a softening of the fruit texture. The rapid deterioration of cut watermelon fruit places both time and space constraints on the retailer. Because cut fruits have a short shelf life, the retailer typically performs the processing on the retail site, and has to monitor the products often to ensure that deteriorating products are discarded.

Unlike the sweetness standards established by the U.S. Department of Agriculture, there are no industry standards to describe the firmness of the edible portions of watermelon fruits. Thus, there are a wide range of descriptors in use, such as "firm" and "crisp" (Erma Zaden catalog descriptors for varieties Gil 104 and Erma 12), "very firm flesh" by Zhang et al. (US Patent Pub. Nos. 2004/0060085 and 2003/0217394) and by *Seminis* Vegetable Seeds, Inc. in their Watermelon catalog to describe the variety Cooperstown. *Seminis* also has described cultivars Fenway, Royal Star, and Sentinel as having "excellent crispness," "firm flesh," and "crisp juicy flesh," respectively. Rogers Seed Company advertises the Tri-X Brand 626 as "exceptionally firm" and the Tri-X Brand 313 as having "a firm texture" and "crispness of flesh."

While advertising terminology used to describe watermelon fruit flesh firmness is quite variable, quantitative measurements show that commercial germplasm prior to this invention have low fruit firmness. Therefore, there is a need in the marketplace for watermelon lines that produce fruits that have a longer shelf life when processed.

SUMMARY OF THE INVENTION

Certain embodiments of the present invention provide for unique watermelon plants with an ultra-firm flesh phenotype and their progeny. In certain embodiments, compositions and methods for producing, breeding, identifying, selecting, and the like of such plants or germplasm are provided. Novel plants of the present invention comprise an introgressed allele locus—located in a genomic region flanked by loci NW0251464 (SEQ ID NO: 1) and NW0250266 (SEQ ID NO: 18)—that is associated with the ultra-firm watermelon flesh phenotype. In certain embodiments, an introgressed allele locus associated with an ultra-firm watermelon flesh phenotype is one flanked by:
  a) loci NW0251464 (SEQ ID NO: 1) and NW0251011 (SEQ ID NO: 12);
  b) loci NW0251464 (SEQ ID NO: 1) and NW0252274 (SEQ ID NO: 10);
  c) loci NW0248953 (SEQ ID NO: 2) and NW0250266 (SEQ ID NO: 18);
  d) loci NW0248953 (SEQ ID NO: 2) and NW0251011 (SEQ ID NO: 12);
  e) loci NW0248953 (SEQ ID NO: 2) and NW0252274 (SEQ ID NO: 10);

f) loci NW0250301 (SEQ ID NO: 3) and NW0250266 (SEQ ID NO: 18);
g) loci NW0250301 (SEQ ID NO: 3) and NW0251011 (SEQ ID NO: 12); or
h) loci NW0250301 (SEQ ID NO: 3) and NW0252274 (SEQ ID NO: 10).

The plants also comprise one or more polymorphic loci comprising alleles or combinations of alleles that are not found in an ultra-firm watermelon flesh variety and that are linked to the locus associated with an ultra-firm watermelon flesh phenotype. Thus, the introgressed allele locus is introduced into a background different from that of a previously existing ultra-firm watermelon flesh variety. In certain embodiments, the introgressed allele locus comprises at least one polymorphic nucleic acid selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments provide for a method of identifying a watermelon plant with a genotype associated with an ultra-firm watermelon flesh phenotype. Such methods include detecting a genotype associated with an ultra-firm watermelon flesh phenotype in a watermelon plant. In certain embodiments a polymorphic nucleic acid is detected in a genomic region flanked by loci NW0251464 (SEQ ID NO: 1) and NW0250266 (SEQ ID NO: 18), or in a sub-region thereof as described herein. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

A watermelon plant that is identified having a genotype associated with an ultra-firm flesh watermelon phenotype can be denoted as comprising a genotype associated with an ultra-firm watermelon flesh phenotype. A watermelon plant, such as a denoted watermelon plant, comprising a genotype associated with an ultra-firm watermelon flesh phenotype can then be selected from a population of plants.

Certain embodiments of the invention provide for a method of producing a watermelon plant having in its genome an introgressed locus associated with an ultra-firm watermelon flesh phenotype. A watermelon plant lacking a locus associated with an ultra-firm watermelon flesh phenotype is crossed with a second watermelon plant that comprises: (a) an allele of at least one polymorphic nucleic acid that is associated with an ultra-firm watermelon flesh phenotype located in a genomic region flanked by loci NW0251464 (SEQ ID NO: 1) and NW0250266 (SEQ ID NO: 18) (or in a sub-region thereof as described herein), and (b) at least one additional polymorphic locus located outside of the region that is not present in said first watermelon plant. From this cross, a population of watermelon plants segregating for the polymorphic locus that is associated with an ultra-firm watermelon flesh phenotype and the additional polymorphic locus is obtained. The polymorphic locus that is associated with an ultra-firm watermelon flesh phenotype is detected in at least one watermelon plant of the population. A watermelon plant can then be selected having the locus associated with an ultra-firm watermelon flesh phenotype that lacks the additional polymorphic locus, thereby obtaining a watermelon plant that comprises in its genome at least one introgressed allele of a polymorphic nucleic acid associated with a firm watermelon flesh phenotype. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments provide for a method of watermelon plant breeding. At least one watermelon that comprises at least one allele of a polymorphic nucleic acid that is genetically linked to a QTL that is flanked by loci NW0251464 (SEQ ID NO: 1) and NW0250266 (SEQ ID NO: 18) and associated with an ultra-firm watermelon flesh phenotype is selected. This watermelon plant is then crossed with itself or a second watermelon plant to produce progeny watermelon plants that have the QTL associated with an ultra-firm watermelon flesh phenotype. In certain embodiments, the at least one polymorphic nucleic acid that is genetically linked to the QTL is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments of the invention provide for a method of introgressing an allele into a watermelon plant. A population of watermelon plants is provided from which at least one watermelon plant is genotyped with respect to at least one polymorphic nucleic acid located in a genomic region flanked by loci NW0251464 (SEQ ID NO: 1) and NW0250266 (SEQ ID NO: 18). At least one watermelon plant is then selected from the population wherein the watermelon plant has at least one allele associated with an ultra-firm watermelon flesh phenotype. In certain embodiments, at least one polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17).

Certain embodiments of the invention provide for a watermelon plant obtained by any of the methods described herein capable of producing a watermelon plant such as by producing, breeding, introgressing, etc., or a progeny plant thereof. Certain embodiments of the invention are drawn to a part of such a plant including, but not limited to pollen, an ovule, a leaf, an embryo, a root, a root tip, an anther, a flower, a fruit, a stem, a shoot, a seed, a protoplast, a cell, or a callus from the plant. Certain embodiments of the invention are drawn to the seed of a watermelon plant obtained by any of the methods described herein capable of producing a watermelon plant such as by producing, breeding, introgressing, etc., or a seed of a progeny plant thereof.

Certain embodiments of the invention provide for an isolated nucleic acid probe or primer that hybridizes under conditions of 5×SSC, 50% formamide, and at 42° C. to a nucleic acid sequence selected from the group consisting of SEQ ID NOs: 1-18 or a fragment thereof, that contains a specific allelic variant. In certain embodiments, the probe or primer is at least 12 nucleotides in length. Certain embodiments of the invention provide for an isolated oligonucleotide comprising a nucleic acid molecule selected from the group consisting of SEQ ID NOs: 1, 2, 3, 4, 5, 6, 7, 8, 9, 10, 11, 12, 13, 14, 15, 16, 17, and 18, and any specific allelic variants thereof. Certain embodiments of the invention provide for an isolated oligonucleotide comprising a nucleic acid fragment of SEQ ID NOs: 1, 2, 3, 4, 5, 6, 7, 8, 9, 10, 11, 12, 13, 14, 15, 16, 17, or 18, that contains a specific allelic variant thereof and that is at least 12 nucleotides in length. Certain embodiments of the invention provide for an isolated oligonucleotide comprising a nucleic acid fragment of SEQ ID NOs: 1, 2, 3, 4, 5, 6, 7, 8, 9, 10, 11, 12, 13, 14, 15, 16, 17, or 18, that contains a specific allelic variant thereof, wherein the fragment that contains said allelic variant is at least 15, at least 18, at least 20, at least 22, at least 25, or at least 30 nucleotides in length.

Further areas of applicability will become apparent from the description provided herein. It should be understood that the description and specific examples are intended for purposes of illustration only and are not intended to limit the scope of the present disclosure.

DETAILED DESCRIPTION

Figure 1:
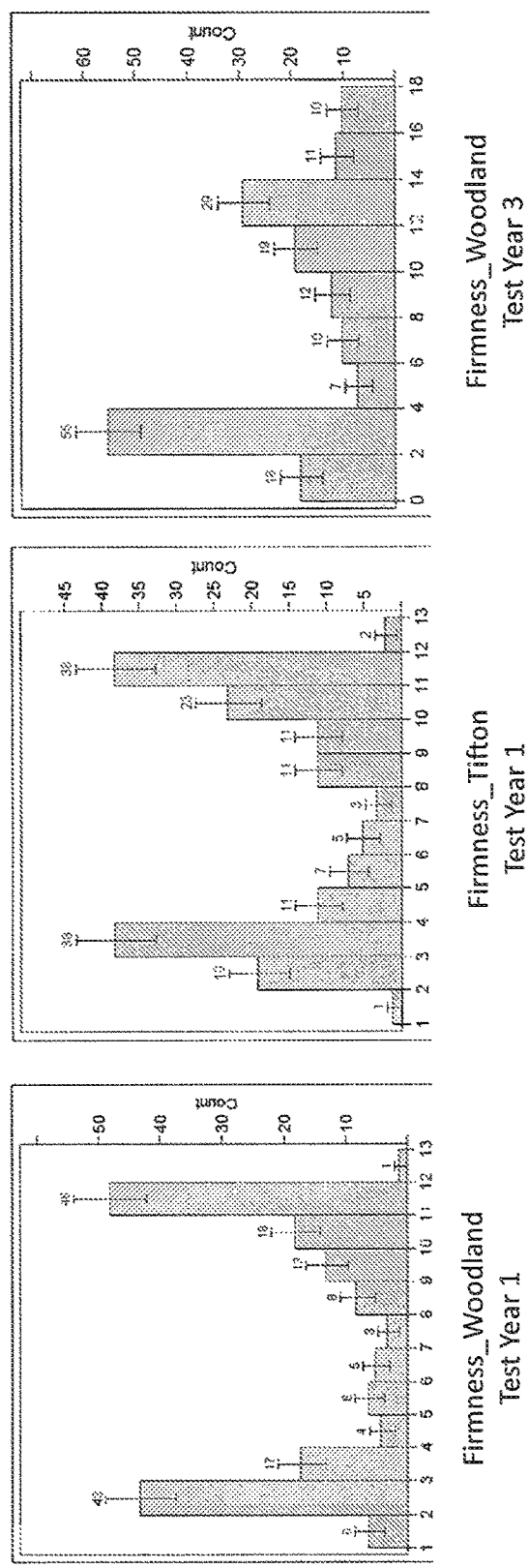
FIG. 1 shows the distributions of firmness phenotypes in three environments tested (Woodland, Calif. Test Year 1 and Test Year 3; Tifton, Ga. Test Year 1).

Headings are provided herein solely for ease of reading and should not be interpreted as limiting.

I. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, having a watermelon "ultra-firm flesh phenotype" means that the edible flesh of a watermelon measures at least about 3.5 pounds force (lb/F) of pressure as evaluated with a penetrometer by methods described herein.

A penetrometer is a device used to measure force, such as used to measure fruit firmness. It can be used to measure both fruit flesh and skin firmness. As used herein, for reported data, a hand-held penetrometer was used with three or five readings on mature fruit, using Penetrometer model FT011 (QA Supplies, Norfolk, Va.) with an 8 millimeter probe (approximately 5/16 inch). Pounds force, or lbf, is the unit read by the penetrometer model FT011, and is provided for readings made exclusively using the 8 millimeter probe.

As used herein, the term "population" means a genetically heterogenous collection of plants that share a common parental derivation.

As used herein, the terms "variety" and "cultivar" mean a group of similar plants that by their genetic pedigrees and performance can be identified from other varieties within the same species.

As used herein, the term "soluble solids" means the percent of solid material found in the edible portion of the fruit. As used herein, soluble solids are measured quantitatively with a refractometer as degrees Brix. Brix is formally defined as weight percent sucrose: if the only soluble solid present in an aqueous solution is sucrose, an actual percentage sucrose will then be measured. However, if other soluble solids are present, as is almost always the case, the reading is not equal to the percentage sucrose, but approximates the overall percentage of soluble solids in the sample. In short, although Brix is technically defined as weight percent sucrose, those of skill in the art recognize that weight percent soluble solids, as obtained with a refractometer, approximate weight percent sucrose and accurately indicates sweetness. Therefore, the higher the percentage soluble solids, as indicated by degree Brix, the higher the perceived sweetness of the fruit.

As used herein, an "allele" refers to one of two or more alternative forms of a genomic sequence at a given locus on a chromosome.

A "Quantitative Trait Locus (QTL)" is a chromosomal location that encodes for alleles that affect the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background. Introgression of a genetic locus can thus be achieved through plant breeding methods and/or by molecular genetic methods.

Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome.

As used herein, the term "maturity" means maturity of fruit development. Maturity indicates the time a watermelon fruit is ready to be harvested. In watermelon, the maturity comes associated with changes in flesh color and sugar content.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

II. Overview

Certain embodiments of the present invention provide for watermelon plants comprising in their genome an introgressed allele locus associated with an ultra-firm watermelon flesh phenotype wherein the introgressed locus allele has not previously been introgressed into the genomic background of a specific variety or cultivar. Certain embodiments provide for methods of detecting in a watermelon plant a genotype associated with an ultra-firm flesh phenotype in a watermelon plant. Certain embodiments provide for methods of identifying and selecting a watermelon plant comprising in its genome a genotype associated with an ultra-firm flesh phenotype. Further, certain embodiments provide for methods of producing a watermelon plant that comprises in its genome at least one introgressed locus associated with an ultra-firm flesh phenotype and methods for introgressing such an allele into a watermelon plant. Watermelon plants and parts thereof made by any of said methods are also provided for in certain embodiments of the invention as well as polymorphic nucleic acid sequences.

The use of markers to infer a phenotype of interest results in the economization of a breeding program by substituting costly, time-intensive phenotyping assays with genotyping. Further, breeding programs can be designed to explicitly drive the frequency of specific favorable phenotypes by targeting particular genotypes (U.S. Pat. No. 6,399,855). Fidelity of these associations may be monitored continuously to ensure maintained predictive ability and, thus, informed breeding decisions (U.S. Patent Pub. No. 2005/0015827).

Successful watermelon production depends on attention to various horticultural practices. These include soil management with special attention to proper fertilization, crop establishment with appropriate spacing, weed control, the introduction of bees for pollination, irrigation, pest management, and if producing fruit from triploid plants, a suitable pollen source for producing seedless (triploid) watermelon. Watermelon fruit size and shape, rind color, thickness and toughness, seed size, color, and number, flesh color, texture, and sugar content, and freedom from fruit defects are all important characteristics to be considered in selection of watermelon varieties. Commercial seed companies typically offer the grower the opportunity to observe these criteria in demonstration plots of their varieties, and some Agricultural Universities provide cultivar analysis data to the local growers (Roberts et al. (2004), Maynard and Sidoti (2003), Schultheis and Thompson (2004), and Leskovar et al. (2004).

Watermelon crops can be established from seed or from transplants. Transplanting has become more common because transplanting can result in an earlier crop compared with a crop produced from direct seeding. When a grower wants to raise a seedless fruited crop, transplanting is preferred. Transplanting helps achieve complete plant stands rapidly, especially where higher seed costs, as with triploid seeds, make direct-seeding risky.

Watermelon is the only economically important cucurbit with pinnatifid (lobed) leaves; all of the other species have whole (non-lobed) leaves. Watermelon growth habit is a trailing vine. The stems are thin, hairy, angular, grooved, and have branched tendrils at each node. The stems are highly branched and up to 30 feet long (Wehner et al. In: Watermelons: Characteristics, Production and Marketing. Maynard, editor. ASHS Press, Alexandria, Va. (2001)).

Watermelon breeders are challenged with anticipating changes in growing conditions, new pathogen pressure, and changing consumer preferences. With these projections, a breeder will attempt to create new cultivars that will fit the developing needs of growers, shippers, retailers, and consumers. Thus, the breeder is challenged to combine in a single genotype as many favorable attributes as possible for good growing distribution and eating.

One important characteristic for the breeder is fruit size. Fruit size is an important consideration because there are different market requirements for particular groups of shippers and consumers. The general categories are: icebox (<12 lb), small (12-18 lb), medium (18-24 lb), large (24-32 lb), and giant (>32 lb). Fruit size is inherited in polygenic fashion, with an estimated 25 genes involved. Fruit is distributed from the grower to the retailer by shippers, who focus with particular weight categories, such as 18-24 lb for seeded and 14-18 lb for seedless. Although historic consumption has been for these sized fruits, there is an increasing trend in the marketplace for a new class of small-fruited watermelon hybrids (with fruit weight between 3-9 lb).

Fruit flesh firmness is another important characteristic. Consumers have varying textural preferences for watermelon fruit, and flesh firmness is correlated with texture. Additionally, fruit firmness is a critical parameter that determines how long cut fruit will last on the retailer's shelf. Cut fruit shelf life research is usually qualitative, with evaluations on when the fruit becomes "slimy" (Perkins-Veazie et al. 1998 HortScience 33:605). A more quantitative evaluation of cut fruit shelf life is to measure the flesh firmness directly using a penetrometer and/or the liquid purge from the cut fruit.

Another important internal fruit characteristic is quality (see Wehner et al. In: Watermelons: Characteristics, Production and Marketing. Maynard, editor. ASHS Press, Alexandria, Va. (2001)). Among the most important of these characteristics is sweetness, measured by Brix, with no bitter taste. Taste panel data demonstrated a direct correlation of good flavor scores with higher Brix levels (Nip et al. (1968) Proc. Amer. Soc. Hort. Sci. 93:547). Brix levels increase as the fruit develops and ripens on the vine. Thus, immature fruits will have unacceptably low sweetness to the consumer; if picked too early, the edible tissue will also not have uniform color. Quantitative recommendations for watermelon fruits have been published. While Wehner et al. suggest Brix levels between 10% and 14% Brix, the United States Department of Agriculture (USDA) has also established fruit quality standards for Brix levels (United States Standards for Grades of Watermelon, U.S. Department of Agriculture (1978)). According to these standards, edible parts of the fruit having not less than 8 Brix are deemed to be "Good," while edible parts of the fruit having not less than 10 Brix are deemed to be "Very Good."

III. Ultra-Firm Flesh Watermelon

Firmness of watermelon flesh is an important fruit quality trait with several benefits for growers, processors, retailers, and customers. Watermelons with firmer flesh have increased field holding, allowing growers to harvest less frequently and/or harvest fruit at a more mature stage (85-95% maturity versus 70% of current market standard). They retain water, nutrients, and flavor during processing; thus having a higher fresh cut yield for processors, lower purge, and longer shelf-life for retailers and consumers. Current marketed watermelon products typically have a firmness of about 2 lb/F, while watermelons with an ultra-firm flesh phenotype have edible flesh that resists a pressure of at least 3.5 lb/F. Table 1 shows flesh firmness data from commercial hybrids and inbred lines.

TABLE 1

Survey of firmness in typical watermelon cultivars and inbred lines. Average firmness readings are in pound force as described herein.

| Line | Origin | Ploidy | Firmness |
|---|---|---|---|
| Tri-X 313 | Syngenta/Rogers | Triploid | 1.4 |
| Millionaire | Harris Moran | Triploid | 1.8 |
| Revolution | SunSeeds | Triploid | 1.7 |
| Majestic | Seminis | Triploid | 1.7 |
| Olympia | Seminis | Triploid | 1.6 |
| Omega | Seminis | Triploid | 1.5 |
| PS110-5288-9 | Seminis | Triploid | 2.3 |
| 4082 | Seminis | Tetraploid | 2 |
| 4084 | Seminis | Tetraploid | 1.5 |
| 4090 | Seminis | Tetraploid | 1.6 |
| 4133 | Seminis | Tetraploid | 2.2 |
| 4134 | Seminis | Tetraploid | 2.4 |
| 4135 | Seminis | Tetraploid | 2.2 |
| 4137 | Seminis | Tetraploid | 2.7 |
| 4138 | Seminis | Tetraploid | 2.2 |
| 47602A | Seminis | Diploid | 1.5 |
| 4203 | Seminis | Diploid | 1.4 |
| Cooperstown | Seminis | Triploid | Firm |
| Fenway | Seminis | Triploid | Firm |
| Royal Star | Seminis | Diploid | Firm |
| Sentinel | Seminis | Diploid | Firm |
| Tri-X Brand 626 | Syngenta/Rogers | Diploid | Firm |
| W-1128 | Seminis | Diploid | Firm |
| W-1119 | Seminis | Diploid | Firm |
| BSI 2532 | Seminis | Diploid | Firm |
| BSI 2527 | Seminis | Diploid | Firm |
| W-2068 | Seminis | Diploid | Firm |
| W-2741 | Seminis | Diploid | Firm |
| W-1488 | Seminis | Diploid | Firm |
| BSI 2543 | Seminis | Diploid | Firm |
| Extazy | Hazera | Triploid | Firm |
| Solitaire | Golden Valley | Triploid | Firm |

It is reported herein that a quantitative trait locus (QTL) with major effects for firmness and single nucleotide polymorphism (SNP) markers in the proximity of this locus have been identified that can be used for the introgression of this genomic region to desirable germplasm, such as by marker-assisted selection and/or marker-assisted backcrossing. A population of plants was obtained from a cross between the watermelon lines 03LB3378-1 and WAS-35-2438. From this population, a linkage map consisting of 19 linkage groups was constructed using 404 polymorphic markers. QTL mapping analysis revealed a major locus controlling flesh firmness on the proximal end of linkage group 9. This discovery of a major firmness QTL will facilitate the development of ultra-firm flesh watermelon products.

Table 2 shows flesh firmness and sugar content from inbred line PI296341, and other various inbred lines created from PI296341 (see U.S. patent application Ser. No. 12/856,286 which is incorporated herein by reference). PI29634 is resistant to *Fusarium wilt*, race 2 pathogen (*Fusarium oxysporum*), and is characterized by having very small round fruits between about 4 and about 6 inches in diameter and weighing between about 1 and about 2.6 pounds. Its fruit flesh is white, very firm, and having low sugars. Organoleptic evaluations of these fruits range from no perception of sweetness to bitter.

TABLE 2

Firmness and sugar content of inbred lines and their PI296341 source. Average firmness readings are in pound force and sugar content is reported as % Brix as described herein.

| Line | Origin | Ploidy | Firmness | Sugar content |
|---|---|---|---|---|
| PI296341 | USDA collection | Diploid | 13.5 | 1.6 |
| 7132 | U.S. application No. 12/856,286 | Triploid | 4.7 | 10.2 |
| 7133 | U.S. application No. 12/856,286 | Triploid | 6.2 | 11.7 |
| 4201 | U.S. application No. 12/856,286 | Diploid | 8 | 9.7 |
| 4203 | U.S. application No. 12/856,286 | Diploid | 7.8 | 10.8 |
| 4204 | U.S. application No. 12/856,286 | Diploid | 6.5 | 9.7 |
| 4207 | U.S. application No. 12/856,286 | Diploid | 6.5 | 10 |

For most breeding objectives, commercial breeders work within germplasm that is often referred to as the "cultivated type." This germplasm is easier to breed with because it generally performs well when evaluated for horticultural performance. The performance advantage the cultivated type provides is sometimes offset by a lack of allelic diversity. This is the tradeoff a breeder accepts when working with cultivated germplasm—better overall performance, but a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, Proc. Am. Soc. Hort. Sci. 44:413-16). In this cross, a nematode disease resistance was transferred from *L. peruvianum* (PI128657) into a cultivated tomato. Despite intensive breeding, it wasn't until the mid-1970's before breeders could overcome the genetic drag and release successful lines carrying this trait. Indeed, even today, tomato breeders deliver this disease resistance gene to a hybrid variety from only one parent. This allows the remaining genetic drag to be masked. The inventiveness of succeeding in this breeding approach has been recognized by the USPTO (U.S. Pat. Nos. 6,414,226, 6,096,944, 5,866,764, and 6,639,132).

In watermelon, the plant introduction accessions are typically lines that produce fruits with undesirable production and eating qualities. Even though these lines have poor horticultural qualities, some watermelon breeders, like some other crop breeders, attempt to breed with these PI lines because they potentially contain novel alleles. To date, the most commonly attempted breeding objective for use of the PI lines is to introgress new disease resistance genes. The process of introgressing novel resistance genes from the PI lines into acceptable commercial types is a long and often arduous process. This process can be difficult because the trait may be polygenic, or have low heritability, or have linkage drag or some combination thereof.

Some phenotypes are determined by the genotype at one locus. These simple traits, like those studied by Gregor Mendel, fall in discontinuous categories such as green or yellow seeds. Most variation observed in nature, however, is continuous, like yield in field corn, or human blood pressure. Unlike simply inherited traits, continuous variation can be the result of polygenic inheritance. Loci that affect continuous variation are referred to as quantitative trait loci (QTLs). Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

Minimally processed watermelon has a short shelf life of 2 to 3 days (Perkins-Veazie et al. (1998) Hortscience 33:605; Wehner et al. in: Watermelons: Characteristics, Production and Marketing. Maynard, editor. ASHA Press, Alexandria, Va. (2001)). Although the maximum shelf life of cut watermelon fruit is only a few days, product quality begins to deteriorate rapidly after being processed. In cut products presented in plastic food containers, the consumer can see this rapid deterioration because liquid will leak out of the cut products and accumulate in the bottom of the container.

Water leakage (also referred to as purge), can be evaluated using the following water retention test. The test is performed at 4° C. To measure liquid loss, the edible portion of the fruits were cut into approximately 1" cubes and weighed. The cube size was chosen because it best approximates the processed product size found in retail outlets. Over a 16 day period, solid samples are re-weighed, and the liquid loss is estimated by calculating the percent weight loss.

Previous experiments have shown that although cut products from standard cultivars may have a shelf life of up to 2 to 3 days, deterioration as measured by water leakage begins almost immediately after cutting. In contrast, firm flesh lines resisted the rapid liquid leakage of the standard watermelon fruits. In certain embodiments of the invention, the cut flesh from the fruit of a watermelon of the invention with a genotype associated with an ultra-firm flesh phenotype loses less than about four percent water after three days storage at 4° centigrade. In certain embodiments of the invention, the cut flesh from the fruit of a watermelon of the invention with a genotype associated with an ultra-firm flesh phenotype loses less than about three percent or less than about two percent water after three days storage at 4° centigrade. Watermelon fruit that retain liquid when cut will achieve a longer period of consumer acceptability after processing in the minimally processed watermelon market.

IV. Genomic Region, QTL, Polymorphic Nucleic Acids, and Alleles Associated with an Ultra-Firm Watermelon Flesh Phenotype Applicants have discovered a genomic region, QTL, alleles, polymorphic nucleic acids, linked markers, and the like that when present in certain allelic forms are associated with an ultra-firm watermelon flesh phenotype. The genomic region is located at the proximal end of watermelon linkage group 9 (of the genetic map of the 03LB3378-1×WAS-35-2438 population) and flanked by loci NW0251464 (SEQ ID NO: 1) and NW0250266 (SEQ ID NO: 18). A major watermelon flesh firmness QTL was found to be located within this region. Certain of the various embodiments of the invention utilize a QTL or polymorphic nucleic acid marker or allele located in this genomic region. Subregions of this genomic region associated with an ultra-firm watermelon flesh phenotype can be described as being flanked by:
  a) loci NW0251464 (SEQ ID NO: 1) and NW0251011 (SEQ ID NO: 12);
  b) loci NW0251464 (SEQ ID NO: 1) and NW0252274 (SEQ ID NO: 10);
  c) loci NW0248953 (SEQ ID NO: 2) and NW0250266 (SEQ ID NO: 18);
  d) loci NW0248953 (SEQ ID NO: 2) and NW0251011 (SEQ ID NO: 12);
  e) loci NW0248953 (SEQ ID NO: 2) and NW0252274 (SEQ ID NO: 10);
  f) loci NW0250301 (SEQ ID NO: 3) and NW0250266 (SEQ ID NO: 18);
  g) loci NW0250301 (SEQ ID NO: 3) and NW0251011 (SEQ ID NO: 12); or
  h) loci NW0250301 (SEQ ID NO: 3) and NW0252274 (SEQ ID NO: 10).

Certain of the various embodiments of the invention utilize a QTL or polymorphic nucleic acid marker or allele located in one or more of these subregions.

Polymorphic nucleic acid markers located within the region flanked by loci NW0251464 (SEQ ID NO: 1) and NW0250266 (SEQ ID NO: 18) include, but are not limited to: NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17). Such markers are believed to be associated with the ultra-firm watermelon flesh phenotype because of their location and proximity to the major firmness QTL. Certain of the various embodiments of the invention utilize one or more polymorphic nucleic acids selected from this group. In certain embodiments, at least two of such markers are used.

The peak of the QTL was found to be in close proximity to at least NW0249132 (SEQ ID NO: 7), NW0248163 (SEQ ID NO: 9), NW0251011 (SEQ ID NO: 12), and NW0250266 (SEQ ID NO:18). To date, NW0250301 (SEQ ID NO: 3), NW0248646 (SEQ ID NO: 5), and NW0252274 (SEQ ID NO:10) have been validated as predictive of the ultra-firm flesh phenotype in diverse watermelon germplasm. In certain of the various embodiments of the invention, at least one polymorphic nucleic acid selected from the group consisting of NW0250301 (SEQ ID NO: 3), NW0248646 (SEQ ID NO: 5), and NW0252274 (SEQ ID NO: 10) is used. In certain embodiments, at least two polymorphic nucleic acids selected from this group are used. In certain embodiments, at least all three of NW0250301 (SEQ ID NO: 3), NW0248646 (SEQ ID NO: 5), and NW0252274 (SEQ ID NO: 10) are used.

In certain embodiments of the invention, it is useful to detect in, or determine whether, a watermelon plant has an allelic state that is associated with an ultra-firm flesh phenotype (Table 3). In certain other embodiments, it is useful to detect in, or determine whether, a watermelon plant has an allelic state that is not associated with an ultra-firm flesh phenotype (Table 3) (The position of the polymorphic site identified in Table 3 for each of these marker sequences is contained in Table 6 and the accompanying Sequence Listing).

In certain embodiments, a plant is identified in which at least one allele at a polymorphic locus associated with an ultra-firm watermelon flesh phenotype is detected. For example, a diploid plant in which the allelic state at a polymorphic locus comprises one allele associated with an ultra-firm watermelon flesh phenotype and one allele that is not associated with an ultra-firm flesh phenotype (i.e., heterozygous at that locus). In certain embodiments of the invention, it may be useful to cross a plant that is heterozygous at a locus associated with an ultra-firm flesh phenotype with a plant that is similarly heterozygous or that does not contain any allele associated with an ultra-firm flesh phenotype at the locus, to produce progeny a certain percentage of plants that are heterozygous at that locus. Plants homozygous at the locus may then be produced by various breeding methods, such as by self-crossing or dihaploidization. In another example, a triploid or tetraploid watermelon plant is identified in which the allelic state at a locus comprises at least one allele associated with an ultra-firm watermelon flesh phenotype wherein other alleles of the locus may or may not also be an allele associated with an ultra-firm watermelon flesh phenotype. Non-limiting exemplary examples include identifying a plant that: has at least one allele of the C allelic state of the polymorphic nucleic acid of NW0252274 (SEQ ID NO: 10); has at least one allele of the C allelic state of the polymorphic nucleic acid of NW0248646 (SEQ ID NO: 5); or has at least one allele of the G allelic state of the polymorphic nucleic acid of NW0250301 (SEQ ID NO: 3); any combination of two of these allelic states, or comprising all three. Certain embodiments include identifying a watermelon plant that: is a diploid plant having one allele of the C allelic state of the polymorphic nucleic acid of NW0252274 (SEQ ID NO: 10) and one allele of the T allelic state of the polymorphic nucleic acid of NW0252274 (SEQ ID NO: 10); is a diploid plant having one allele of the C allelic state of the polymorphic nucleic acid of NW0248646 (SEQ ID NO: 5) and one allele of the A allelic state of the polymorphic nucleic acid of NW0248646 (SEQ ID NO: 5); or is a diploid plant having one allele of the G allelic state of the polymorphic nucleic acid of NW0250301 (SEQ ID NO: 3) and one allele of the A allelic state of the polymorphic nucleic acid of NW0250301 (SEQ ID NO: 3); any combination of two of these allelic states, or comprising all three. One of skill in the art will also recognize that it can be useful to identify at a genetic locus a polymorphic nucleic acid marker that is not associated with an ultra-firm watermelon flesh phenotype in a plant, such as when introgressing a QTL associated with an ultra-firm watermelon flesh phenotype into a genetic background not associated with such a phenotype.

In certain embodiments, a plant is identified in which at least two alleles associated with an ultra-firm watermelon flesh phenotype at a locus are detected. For example, a diploid plant in which both allelic states at a polymorphic locus are associated with an ultra-firm watermelon flesh phenotype (i.e., homozygous at that locus). For example, a triploid or tetraploid watermelon plant in which the allelic state comprises at least two alleles at a locus that are associated with an ultra-firm watermelon flesh phenotype, wherein other alleles at the locus may or may not also be an allele associated with an ultra-firm watermelon flesh phenotype. Certain non-limiting exemplary examples include identifying: a diploid watermelon plant that has the CC allelic state of the polymorphic nucleic acid of NW0248646 (SEQ ID NO: 5); a diploid watermelon plant that has the CC allelic state of the polymorphic nucleic acid of NW0248646 (SEQ ID NO: 5); or a diploid watermelon plant that has the GG allelic state of the polymorphic nucleic acid of NW0250301 (SEQ ID NO: 3); any combination of two of these allelic states, or the plant comprises all three.

The above markers and allelic states are exemplary. From Table 3, one of skill in the art would recognize how to identify watermelon plants with other polymorphic nucleic acid markers and allelic states thereof related to watermelon firmness consistent with the present invention. One of skill in the art would also know how to identify the allelic state of other polymorphic nucleic acid markers located in the genomic region(s) or linked to the QTL or other markers identified herein, to determine their association with watermelon firmness.

TABLE 3

Genetic positions* and alternate allelic states of polymorphic nucleic acid markers of the invention indicating the allelic state associated with the ultra-firm watermelon flesh QTL.

| Marker Name | SEQ ID NO: | Linkage Group | Genetic Map position (cM) | Allele 1 (non-firm flesh) | Allele 2 (ultra-firm flesh phenotype QTL-associated) |
|---|---|---|---|---|---|
| NW0251464 | 1 | 2 | 122.4666304 | A or G | deletion, absence of allele |
| NW0248953 | 2 | 2 | 131.6920961 | A | T |
| NW0250301 | 3 | 2 | 134.2525663 | A | G |
| NW0248949 | 4 | 2 | 136.2284633 | G | A |
| NW0248646 | 5 | 2 | 136.9855946 | A | C |
| NW0249077 | 6 | 2 | 136.9855946 | A or C | deletion, absence of allele |
| NW0249132 | 7 | 2 | 136.9920737 | T or C | deletion, absence of allele |
| NW0252494 | 8 | 2 | 137.6844216 | T or C | deletion, absence of allele |
| NW0248163 | 9 | 2 | 138.2842599 | A or C | deletion, absence of allele |
| NW0252274 | 10 | 2 | 138.5377262 | T | C |
| NW0248905 | 11 | 2 | 138.7747985 | A | G |
| NW0251011 | 12 | 2 | 138.7747985 | C | T |
| NW0248869 | 13 | 2 | 139.8297546 | T | G |
| NW0251470 | 14 | 2 | 139.8297546 | A | T |
| NW0251308 | 15 | 2 | 144.5711848 | C | T |
| NW0250718 | 16 | 2 | 145.8088579 | C | T |
| NW0248059 | 17 | 2 | 152.2083556 | G | A |
| NW0250266 | 18 | 2 | 157.6817827 | T | C |

*Linkage group 9 from the genetic map of the 03LB3378-1 × WAS-35-2438 derived population was aligned to linkage group 2 of a consensus watermelon SNP map constructed with three additional segregating populations. In Table 3, the genetic map positions represent positions on linkage group 2 of the consensus watermelon SNP map.

Like humans, watermelons are natural diploids, having their chromosomes arranged in pairs. Watermelon plants, however, can undergo a duplication of their entire set of chromosomes and exist as tetraploids. While it is uncommon for watermelons to produce spontaneous tetraploids, this process can be routinely produced in the laboratory using cell biology techniques. Triploid seeds can be produced by crossing a tetraploid parent by a diploid parent. When triploid plants are grown, seed formation in the fruit aborts because of the ploidy level differences, resulting in seedless fruits.

In certain embodiments of methods of the invention, a male parent diploid plant is homozygous for the QTL or a polymorphic nucleic acid marker allele associated with the firm watermelon flesh phenotype. The male parent diploid is crossed with a female tetraploid lacking the QTL or a polymorphic nucleic acid marker allele associated with the firm watermelon flesh phenotype, to produce triploid hybrid progeny. This results in one copy of the QTL or polymorphic marker allele associated with the firm watermelon flesh phenotype (from the diploid parent) and two non-QTL/ marker alleles (from the tetraploid parent) in the triploid hybrid.

Certain embodiments of the invention contemplate the use of dihaploidization to produce an inbred line. A haploid plant has only one copy of each chromosome instead of the normal pair of chromosomes in a diploid plant. Haploid plants can be produced, for example, by treating with a haploid inducer. Haploids plants can be subjected to treatment that causes the single copy chromosome set to double, producing a duplicate copy of the original set. The resulting plant is termed a "double-haploid" and contains pairs of chromosomes that are generally in a homozygous allelic state at any given locus. Dihaploidization can reduce the time required to develop new inbred lines in comparison to developing lines through successive rounds of backcrossing.

As used herein, in a diploid plant, a homozygous allelic state is represented as AA, CC, GG, or TT, where the designated polymorphic position of the allele comprises alternate nucleotide bases. As used herein, in a diploid plant, a homozygous allelic state is represented as DD, where the designated polymorphic position of the allele comprises a deletion of one or more bases in comparison to an alternate allele.

One of skill in the art would understand that additional polymorphic nucleic acids that are located in the genomic regions identified may be used in certain embodiments of the methods of the invention. Given the provisions herein of a genomic region, QTL, and polymorphic markers identified herein, additional markers located either within or near this genomic region that are associated with the phenotype can be obtained by typing new markers in various germplasm. The genomic region, QTL, and polymorphic markers identified herein can also be mapped relative to any publically available physical or genetic map to place the region described herein on such map. One of skill in the art would also understand that additional polymorphic nucleic acids that are genetically linked to the QTL associated with a firm watermelon flesh phenotype and that map within 40 cM, 20 cM, 10 cM, 5 cM, or 1 cM of the QTL associated with a firm watermelon flesh phenotype may also be used.

IV. Introgression of a Genomic Locus Associated with a Firm Flesh Phenotype

Provided herein are unique watermelon germplasms or watermelon plants comprising an introgressed genomic region that is associated with a firm watermelon flesh phenotype and method of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (e.g., a firm watermelon flesh phenotype germplasm) and both linked and unlinked markers characteristic of the desired genetic background of a second germplasm. Flanking markers that identify a genomic region associated with a firm watermelon flesh phenotype are loci NW0251464 (SEQ ID NO: 1) and NW0250266 (SEQ ID NO: 18), and those that identify sub-regions thereof include, but are not limited to:
 a) loci NW0251464 (SEQ ID NO: 1) and NW0251011 (SEQ ID NO: 12);
 b) loci NW0251464 (SEQ ID NO: 1) and NW0252274 (SEQ ID NO: 10);
 c) loci NW0248953 (SEQ ID NO: 2) and NW0250266 (SEQ ID NO: 18);
 d) loci NW0248953 (SEQ ID NO: 2) and NW0251011 (SEQ ID NO: 12);
 e) loci NW0248953 (SEQ ID NO: 2) and NW0252274 (SEQ ID NO: 10);
 f) loci NW0250301 (SEQ ID NO: 3) and NW0250266 (SEQ ID NO: 18);
 g) loci NW0250301 (SEQ ID NO: 3) and NW0251011 (SEQ ID NO: 12); and
 h) loci NW0250301 (SEQ ID NO: 3) and NW0252274 (SEQ ID NO: 10).

Flanking markers that fall on both the telomere proximal end and the centromere proximal end (such as those provided herein) of any of these genomic intervals may be useful in a variety of breeding efforts that include, but are not limited to, introgression of genomic regions associated with an ultra-firm watermelon flesh phenotype into a genetic background comprising markers associated with germplasm that ordinarily contains a genotype associated with a non-firm flesh phenotype. Markers that are linked and either immediately adjacent or adjacent to the identified ultra-firm watermelon flesh phenotype QTL that permit introgression of the QTL in the absence of extraneous linked DNA from the source germplasm containing the QTL are provided herewith. Those of skill in the art will appreciate that when seeking to introgress a smaller genomic region comprising a QTL associated with an ultra-firm watermelon flesh phenotype described herein, that any of the telomere proximal or centromere proximal markers that are immediately adjacent to a larger genomic region comprising the QTL can be used to introgress that smaller genomic region.

Watermelon plants or germplasm comprising an introgressed region that is associated with an ultra-firm watermelon flesh phenotype wherein at least 10%, 25%, 50%, 75%, 90%, or 99% of the remaining genomic sequences carry markers characteristic of plant or germplasm that otherwise or ordinarily comprise a genomic region associated with an non-ultra-firm flesh phenotype, are thus provided. Furthermore, watermelon plants comprising an introgressed region where closely linked regions adjacent and/or immediately adjacent to the genomic regions, QTL, and markers provided herewith that comprise genomic sequences carrying markers characteristic of watermelon plants or germplasm that otherwise or ordinarily comprise a genomic region associated with the phenotype are also provided.

V. Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

As a set, polymorphic markers serve as a useful tool for fingerprinting plants to inform the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a watermelon plant a genotype associated with a firm watermelon flesh phenotype, identify a watermelon plant with a genotype associated with a firm watermelon flesh phenotype, and to select a watermelon plant with a genotype associated with a firm watermelon flesh phenotype. In certain embodiments of methods of the invention, polymorphic nucleic acids can be used to produce a watermelon plant that comprises in its genome an introgressed locus associated with a firm watermelon flesh phenotype. In certain embodiments of the invention, polymorphic nucleic acids can be used to breed progeny watermelon plants comprising a locus associated with a firm watermelon flesh phenotype.

Certain genetic markers useful in the present invention include "dominant" or "codominant" markers. "Codominant" markers reveal the presence of two or more alleles (two per diploid individual). "Dominant" markers reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a firm watermelon flesh phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

EXAMPLES

The following disclosed embodiments are merely representative of the invention which may be embodied in various forms. Thus, specific structural, functional, and procedural details disclosed in the following examples are not to be interpreted as limiting.

Example 1: Firm Flesh Watermelon

Firm flesh watermelon accessions have been identified in different species and varieties of the genus *Citrullus*, including *C. colocynthis*, *C. lanatus* var. *citroides*, and *C. lanatus* var. *lanatus*. PI296341 is a *C. lanatus* var. *citroides* accession originating from Africa available through the Germplasm Resources Information Network. PI296341 was backcrossed for several generations to all sweet type elite inbred lines (*C. lanatus* var. *lanatus*) to derive the ultra-firm flesh watermelon line 03LB3387-1.

A segregating population was developed from the cross of 03LB3387-1 and WAS-35-2438 by single seed descent for the mapping of the ultra-firm flesh trait. The population 03LB3387-1×WAS-35-2438 consisted of 186 F4:5 lines and was planted in three environments: Woodland, Calif. and Tifton, Ga. Test Year 1, and Woodland, Calif. in Test Year 3. The two experiments in Woodland, Calif., were planted in randomized complete block designs, while the Test Year 1 trial in Tifton was a complete randomized design. The parental lines 03LB3387-1 and WAS-35-2438 and their F1 hybrid were used as controls in each of the three trials. Firmness, total soluble solids (Brix), and lycopene data was collected in the Woodland and Tifton Test Year 1 trials. Firmness and Brix data was collected in Woodland in Test Year 3. Firmness data was collected as three penetrometer readings per fruit. The goal was to position readings longitudinally in the proximal, middle, and distal thirds of each fruit, and transversely mid-way between the rind and the center. Brix values were measured with a hand held refractometer (Atago, model PAL-1) using juice extracted with a citrus juicer from fruit samples (~11.5 $cm^3$) with mature-red color. Lycopene content was quantified by HPLC using a bulk of 4 to 5 core samples (~21 $cm^3$ each) taken from multiple flesh positions of fruit with mature-red color. Data was obtained in Test Year 1 using a penetrometer with a maximum reading of 12 lb/F; therefore, it is possible that for the Test Year 1 trials, a reported value of 12 may actually represent a value greater than 12 lb/F. During the Test Year 3 trial, data was obtained with an instrument that had a range of readings from 1 to 30 lb/F. Therefore, data for each of the three trials was analyzed separately instead of deriving phenotypic means and conducting QTL mapping analysis across the three environments.

Least square means for firmness, Brix, and lycopene content were generated for each family in each of three environments. Firmness phenotypes showed a bimodal distribution, implying that a single major QTL segregates for firmness in the mapping population (FIG. 1). The parental lines 03LB3387-1 and WAS-35-2438 and their F1 hybrid showed consistent phenotypes across locations and years (Table 4).

TABLE 4

Phenotypic means for firmness, Brix, and lycopene content of parental lines (03LB3387-1 and WAS-35-2438) and their F1 hybrid for each of the three trials.

| | Woodland Test Year 1 | | | Tifton Test Year 1 | | | Woodland Test Year 3 | |
|---|---|---|---|---|---|---|---|---|
| | Firmness | Brix | Lycopene | Firmness | Brix | Lycopene | Firmness | Brix |
| O3LB3387 | 10.98 | 9.00 | 49.68 | 10.59 | 8.85 | 44.70 | 11.67 | 9.04 |
| WAS-35-2438 | 2.11 | 10.18 | 61.33 | 2.43 | 11.68 | 67.00 | 2.15 | 10.64 |
| F1 | 7.59 | 9.87 | 62.26 | 8.08 | 10.88 | 79.24 | 6.10 | 10.29 |

One-hundred and eighty six 03LB3387-1×WAS-35-2438 lines were genotyped at the F4 generation using 1,536 SNP markers. A linkage map of the segregating population was constructed using 404 polymorphic markers with JoinMap software. The genetic map consisted of 19 linkage groups ranging in length from 4.5 to 142.1 cM, and had an average length of 64.1 cM. The average distance between adjacent SNP markers across the 19 linkage groups was 3.9 cM.

Figure 2:
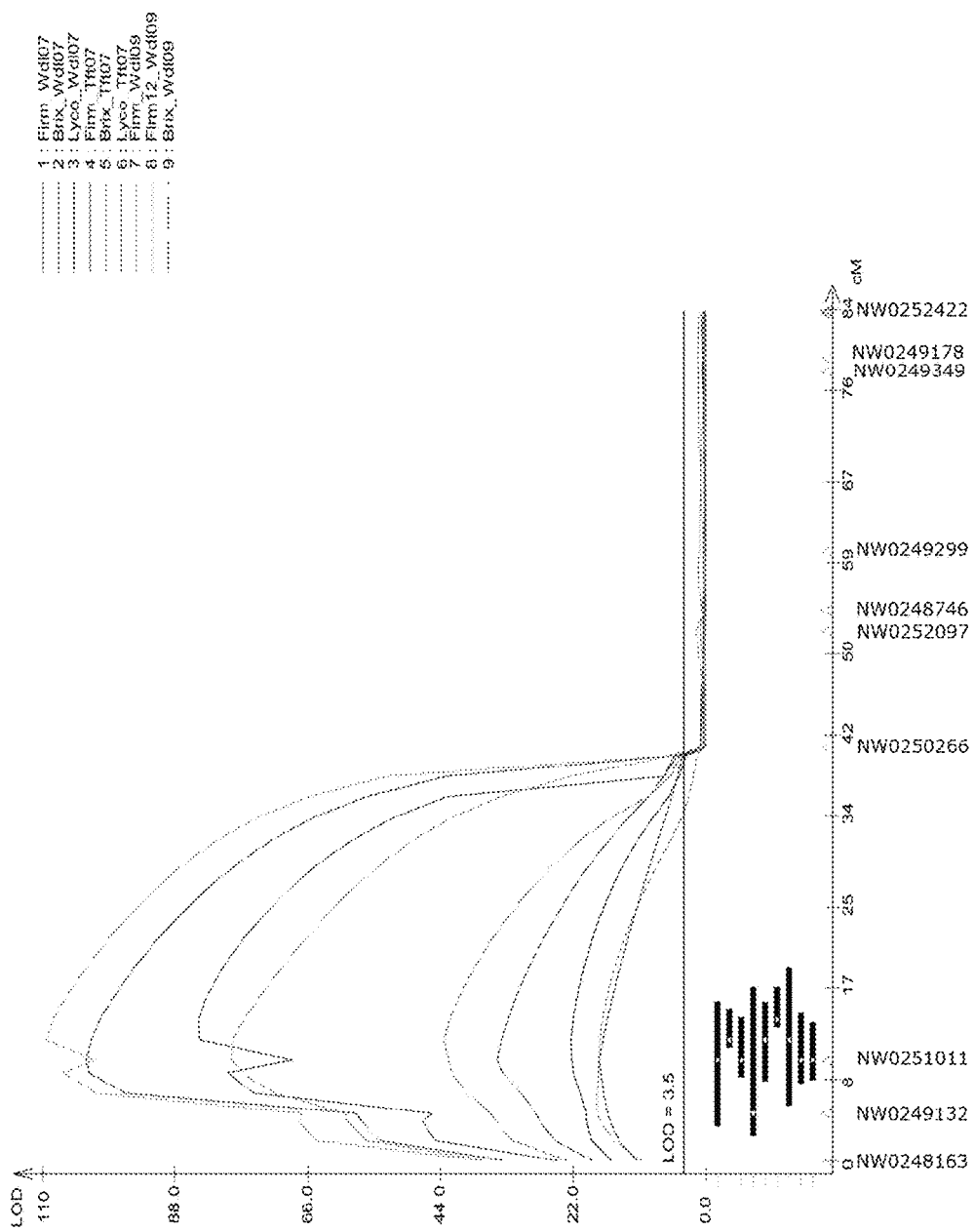
FIG. 2 shows the major firmness QTL identified on linkage group 9 (of the genetic map of the 03LB3378-1× WAS-35-2438 derived population) and co-localized QTL for Brix and lycopene content identified using QTL Cartographer. Black bars show the QTL curves correspond to the 2-LOD confidence intervals and white squares on each bar identify the QTL peaks.

QTL mapping analysis using composite interval mapping in QTL Cartographer identified a major locus controlling firmness on the proximal end of linkage group 9 ([FIG. 2). QTL for Brix and lycopene content were also mapped in the same genomic interval and had moderate to low QTL effects (Table 5).

TABLE 5

QTL identifiers for firmness, Brix, and lycopene content on linkage group 9 of the genetic map of the 03LB3378-1 x WAS-35-2438 derived population. Position of the QTL on the linkage group (cM), additive and dominance effects of the QTL and 2-LOD confidence intervals are reported. (Woodland, CA Test Year 1 (Wdl1); Tifton, GA Test Year 1 (Tft1); Woodland, CA Test Year 3 (Wdl3)).

| Traits | cM | Additive effect | Dominance effect | 2-LOD left | 2-LOD right |
|---|---|---|---|---|---|
| Firmness_Wdl1 | 9.9 | 4.0051 | 0.4522 | 8.2 | 13.4 |
| Firmness_Tft1 | 13.9 | 3.6203 | 0.1133 | 13.4 | 16.9 |
| Firmness_Wdl3 | 9.9 | 5.2477 | −0.7243 | 8.5 | 13.9 |
| Brix_Wdl1 | 9.9 | −0.8533 | 0.0026 | 7.9 | 14.3 |
| Brix_Tft1 | 11.9 | −1.3193 | 0.1075 | 8.1 | 15.4 |
| Brix_Wdl3 | 9.9 | −0.6574 | 0.2705 | 3.7 | 15.5 |
| Lycopene_Wdl1 | 11.9 | −11.2121 | 0.9482 | 5.7 | 18.8 |
| Lycopene_Tft1 | 4.7 | −9.1304 | −20.594 | 2.7 | 16.9 |

Figure 3A:
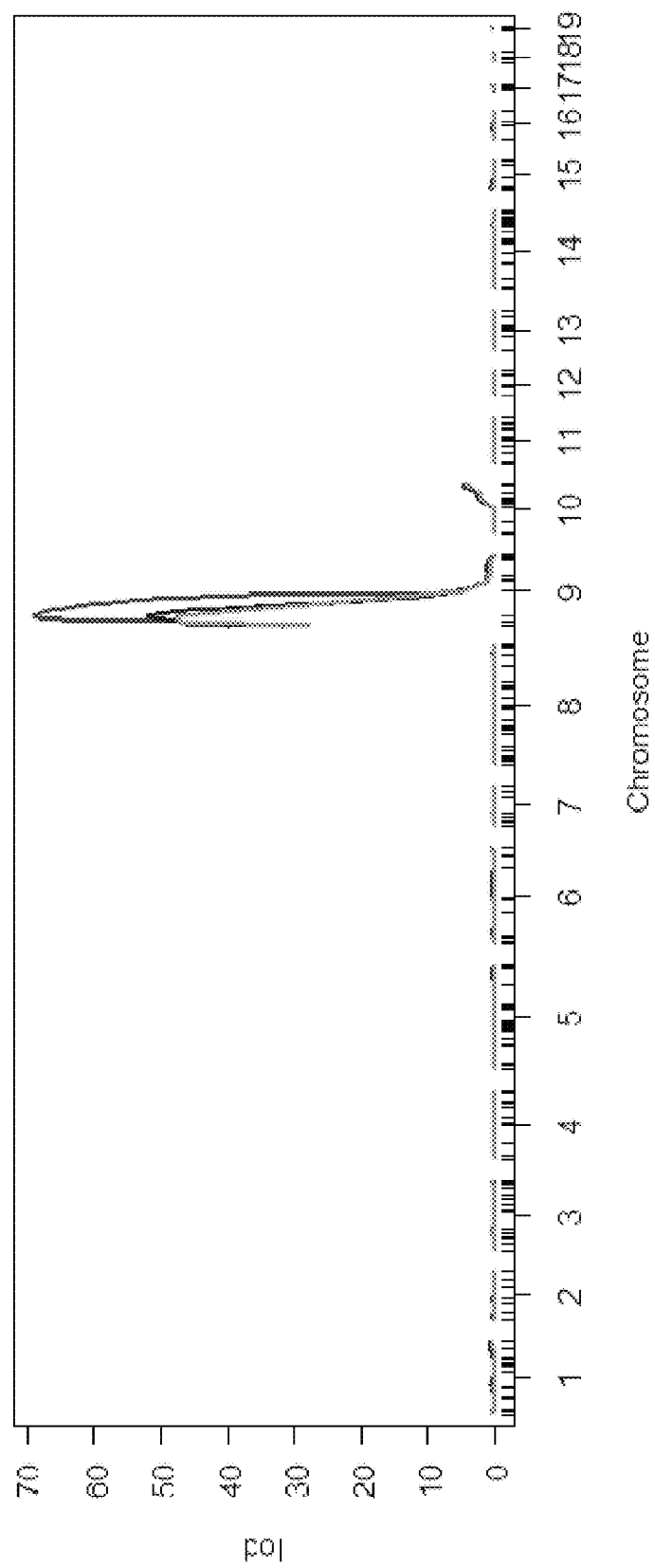
FIG. 3A The graph shows overlay of LOD curves of single-QTL genome scans conducted by three interval mapping methods (EM algorithm), Haley-Knott regression and multiple imputations for the 19 linkage groups of the 03LB3387×WAS-35-2438 genetic map.
Figure 3B:
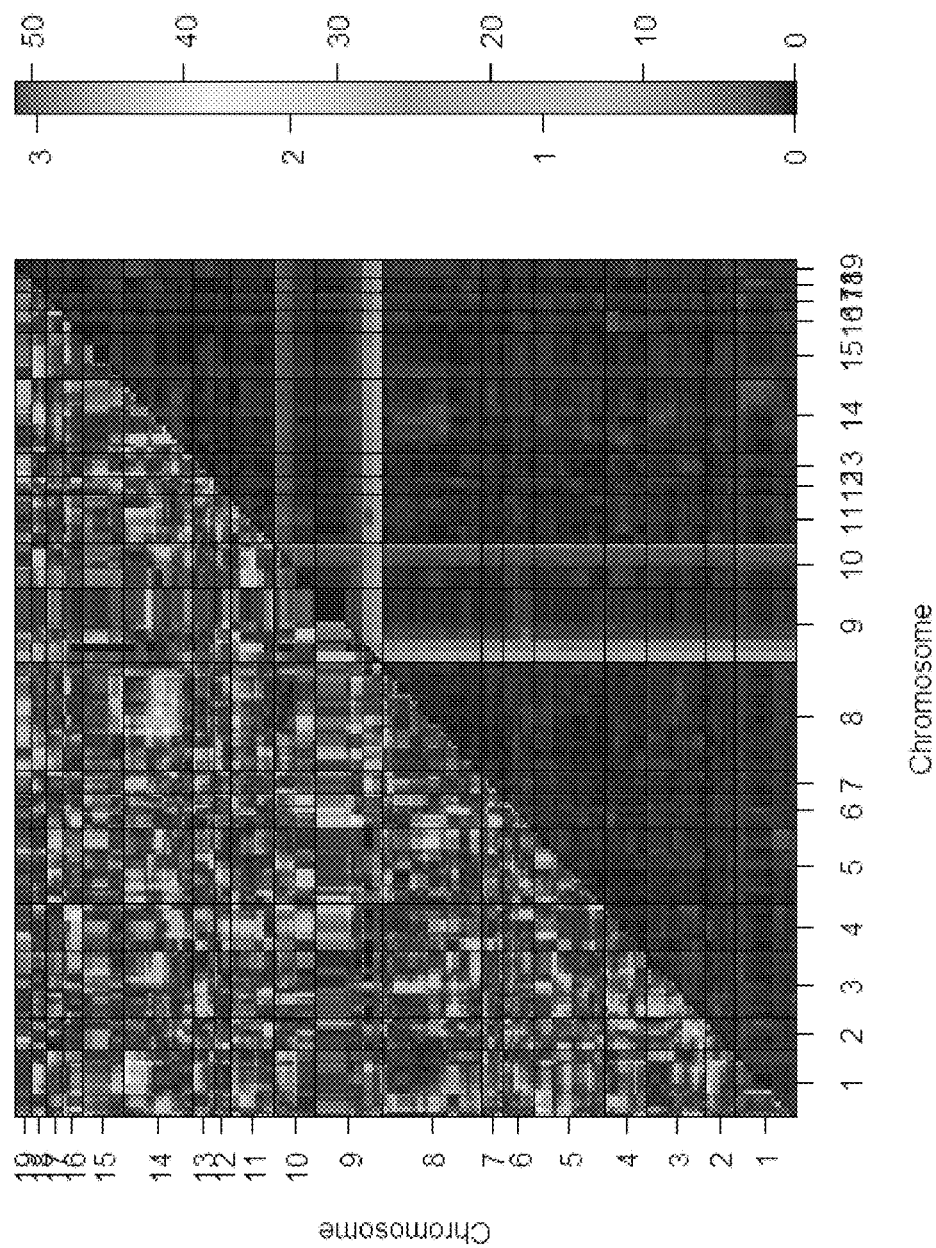
FIG. 3B The heat plot corresponds to two-QTL genome scans and shows the main effect for firmness identified on linkage group 9 below the diagonal and the lack of two-locus epistatic interactions above the diagonal.

The QTL were consistent across the three environments trialed and their 2-LOD intervals overlapped (FIG. 2; Table 5). Results were also confirmed with single- and two-QTL genome scans in Rqtl (FIG. 3A and FIG. 3B) (The analysis presented in FIG. 3B uses phenotypic data of the Woodland Test Year 1 trial. Analysis was also conducted and had similar results using phenotypic data of Tifton Test Year 1 and Woodland Test Year 3 trials). The QTL for flesh firmness was localized to the genomic region flanked by NW0251464 (SEQ ID NO: 1) and NW0250266 (SEQ ID NO: 18), and the peak of the QTL was in close proximity to NW0251011 (SEQ ID NO: 12), NW0249132 (SEQ ID NO: 7), NW0248163 (SEQ ID NO: 9), and NW0250266 (SEQ ID NO: 18). Linkage group 9 from the genetic map of the 03LB3378-1×WAS-35-2438 population was later aligned to linkage group 2 of a consensus watermelon SNP map constructed with three additional segregating populations (Table 3). Additional markers were identified within the QTL interval including: NW0248953 (SEQ ID NO:2); NW0250301 (SEQ ID NO: 3), NW0248949 (SEQ ID NO: 4), NW0248646 (SEQ ID NO: 5), NW0249077 (SEQ ID NO: 6), NW0252494 (SEQ ID NO: 8), NW0252274 (SEQ ID NO: 10]), NW0248905 (SEQ ID NO: 11), NW0248869 (SEQ ID NO: 13), NW0251470 (SEQ ID NO: 14), NW0251308 (SEQ ID NO: 15), NW0250718 (SEQ ID NO: 16), and NW0248059 (SEQ ID NO: 17). The markers NW0252274 (SEQ ID NO: 10), NW0248646 (SEQ ID NO: 5), and NW0250301 (SEQ ID NO: 3) were found to predict the firm flesh phenotype accurately in diverse watermelon germplasm.

TABLE 6

Sequences of certain polymorphic nucleic acid markers in proximity to a QTL locus associated with an ultra-firm flesh phenotype.

| Marker Name | SEQ ID NO: | Polymorphic Position | Sequence |
|---|---|---|---|
| NW0251646 | 1 | 61 | gacaactgcaagagaattttc aacatgaaacattcttcagcaag gaatgttatcgagc[a/g]agcg tttgggttgctaaagcagcagtg ggctattcttagtgaaacataat tctatccaa |
| NW0248953 | 2 | 61 | ttgaaagttattcgtttactgaa tgatgaggcgattggcatatcaa aagtctcctttatt[a/t]gacg aggctaagagttgtggatatgat ctggaagttgtctctttctctca tattcgttat |
| NW0250301 | 3 | 61 | ggtggaactaagctcgacaacaa tgagcatcaacctaccgagcgag aaggcactattgcg[a/g]ttag caacatggaaaagtagtcctgat cttcgttctcgtgtagactatgt cttaggactt |
| NW0248949 | 4 | 61 | ggactccagccagaacatagaca tcccccacccccatctgaaaaac taatattgtcccca[a/g]tgtg agaaaagaaaanaagagcatggg acaaatgagaagggaaacaaaga acttccctga |
| NW0248646 | 5 | 61 | tcaacaataaccctagagaagac cttaacaaacacttgaaggattt tcacatctgaggac[a/c]tttc cattctctttgaaggatggacaa atgattggttgtactatcaacct cctggatcga |
| NW0249077 | 6 | 45 | tgcaggtatccttatgatctgaa atatcatcaagattacactta [a/c]tcgcttgaataatcagaa atttcaaagtgttattttacctg taatcttcaaaaagaagca |
| NW0249132 | 7 | 61 | aggataaacaaattcacatacac ttttcccaaatacatttaaaagg aaaattggagaggg[t/c]caaa taagtcaagaggctaagctgtaa tgaatataacagctttgttcaag ttaaaccaat |
| NW0252494 | 8 | 61 | acaaaattctttccaaaaatgta aaattctcaattatggaaagttg gcgccgcgatgcta[t/c]tggc |

TABLE 6-continued

Sequences of certain polymorphic nucleic acid markers in proximity to a QTL locus associated with an ultra-firm flesh phenotype.

| Marker Name | SEQ ID NO: | Poly-morphic Position | Sequence |
|---|---|---|---|
| | | | tagagccgcggtgctgtgcgtca tgcaaacctaccctcggcgctgt gccgcagcg |
| NW0248163 | 9 | 61 | gaaatttaggccacccacatgcc ttcttcgagtccttcagcattgg gggttatctttgta[a/c]tcga gttacccacatgccttgtccgag tccttcaacattgggaaccattt ctatatctcg |
| NW0252274 | 10 | 61 | cttctcggaaatacttcatctct atggacatcaccttccttgagga taaaccctttctttc[t/c]cgtt agtcctcgtcagggagagagtag tagtgaagagactaactgttcat caccttcaa |
| NW0248905 | 11 | 61 | ggtcacagattcaatctctaaag ttgtatgccaccaaacttagaac ctgcaattactacg[a/g]attt gacatccatataccacacaaatgaa tctacacgtttgttgttttnaat gaactaaaaa |
| NW0251011 | 12 | 61 | atattcgagttggccaaataggt aacttattattttcttgagtttg ttaacatgataata[t/c]tact caacgaaatcctatgatagctac acatttgagaatgcataaacaaa ctcgtattg |
| NW0248869 | 13 | 61 | aaaattttatgtacaggctgtta cagttcgtcctttatctgctgtc agctccctcgtacg[t/g]tttg cagaggagccccagatgtttgcc attgaattact |
| NW0251470 | 14 | 61 | gtttggaactgttatatccccnt aaactgctcaatgttatctcaga gtgagcttctacca[a/t]taaa gctccttgttctggtnccaaaaa |

TABLE 6-continued

Sequences of certain polymorphic nucleic acid markers in proximity to a QTL locus associated with an ultra-firm flesh phenotype.

| Marker Name | SEQ ID NO: | Poly-morphic Position | Sequence |
|---|---|---|---|
| | | | acacttccaccttccnattttn ggtctctct |
| NW0251308 | 15 | 61 | caattgctgcagatgtaactgaa agaacaatcaangttctaggatg gcatcattttgagt[t/c]tagt ttcctaataaagtgttcatctgt gttttngatgtgctaaatcagtg gaggcnttt |
| NW0250718 | 16 | 61 | tgacggcggttgctgcattgctc atggctgtatggttcatgtctac gattggatgctcga[t/c]gaac accctccgatcaatctcgattat cagcgagtcaacgatgttgggtg gatcgatgct |
| NW0248059 | 17 | 61 | acttaattgaatctaatagatga agttcaattacgcaagtacaaaa anttactagttaat[a/g]tgtc atacacgcaagtcaaagatcttt atgcatggtgcctccaatttgtt atcagagacc |
| NW0250266 | 18 | 61 | gtatcttttgtgtccgtattagc ttgcgacctcttcgagtggttat agttaggttgtacg[t/c]tttg atgttttctatgttggtatgag tggcttggggattcttttcggag cattcatgtt |

Polymorphic nucleotide bases are designated in the Sequence Listing provided herewith according to the WIPO Standard ST.25 (1998), Table 1, as follows: r=g or a (purine); y=t/u or c (pyrimidine); m=a or c; (amino); k=g or t/u (keto); s=g or c (strong interactions 3H-bonds); w=a or t/u (weak interactions 2H-bonds); b=g or c or t/u (not a); d=a or g or t/u (not c); h=a or c or t/u (not g); v=a or g or c (not t, not u); and n=a or g or c or t/u (unknown, or other; any.) Deletions are also indicated as provided in Table 3.

What is claimed is:

1. A method of detecting in at least one watermelon plant a genotype linked with an ultra-firm watermelon flesh phenotype, the method comprising the steps of:
   (i) detecting by genotyping in at least one watermelon plant a molecular marker that is linked within 10 cM to an allele present in at least one polymorphic nucleic acid selected from the group consisting of NW0250301 (SEQ ID NO: 3), NW0248646 (SEQ ID NO:5), and NW0252274 (SEQ ID NO:10) and linked with an ultra-firm watermelon flesh phenotype;
   (ii) selecting said at least one watermelon plant comprising a molecular marker that is linked within 10 cM to said allele present in at least one polymorphic nucleic acid selected from the group consisting of NW0250301 (SEQ ID NO: 3), NW0248646 (SEQ ID NO:5), and NW0252274 (SEQ ID NO:10) and linked with an ultra-firm watermelon flesh phenotype; and
   (iii) crossing said selected at least one watermelon plant to produce progeny comprising a molecular marker that is linked within 10 cM to said allele present in at least one polymorphic nucleic acid selected from the group consisting of NW0250301 (SEQ ID NO: 3), NW0248646 (SEQ ID NO:5), and NW0252274 (SEQ ID NO:10) and linked with an ultra-firm watermelon flesh phenotype.

2. The method of claim 1, wherein the polymorphic nucleic acid is located in a genomic region flanked by:
   a) loci NW0248953 (SEQ ID NO: 2) and NW0250718 (SEQ ID NO: 16);
   b) loci NW0248953 (SEQ ID NO: 2) and NW0251011 (SEQ ID NO: 12);
   c) loci NW0248953 (SEQ ID NO: 2) and NW0252274 (SEQ ID NO: 10);
   d) loci NW0250301 (SEQ ID NO: 3) and NW0250718 (SEQ ID NO:16);
   e) loci NW0250301 (SEQ ID NO: 3) and NW0251011 (SEQ ID NO: 12); or
   f) loci NW0250301 (SEQ ID NO: 3) and NW0252274 (SEQ ID NO: 10).

3. The method of claim 1, wherein at least one of said polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), and NW0250718 (SEQ ID NO: 16).

4. The method of claim 1, wherein the genotype linked with an ultra-firm watermelon flesh genotype comprises having at least one of: at least one allele of the C allelic state of the polymorphic nucleic acid of NW0252274 (SEQ ID NO: 10); at least one allele of the C allelic state of the polymorphic nucleic acid of NW0248646 (SEQ ID NO: 5); or at least one allele of the G allelic state of the polymorphic nucleic acid of NW0250301 (SEQ ID NO: 3).

5. A method for introgressing a locus linked with an ultra-firm watermelon flesh phenotype into a watermelon plant, the method comprising:
   (i) crossing a first watermelon plant lacking a locus linked with an ultra-firm watermelon flesh phenotype with a second watermelon plant comprising: (a) a molecular marker that is linked within 10 cM to an allele present in at least one polymorphic nucleic acid selected from the group consisting of NW0250301 (SEQ ID NO: 3), NW0248646 (SEQ ID NO:5), and NW0252274 (SEQ ID NO:10), and (b) at least one additional polymorphic locus that is not present in said first watermelon plant and is located greater than 10 cM from said allele present in at least one polymorphic nucleic acid, to obtain a population of watermelon plants segregating for the polymorphic locus that is linked with an ultra-firm watermelon flesh phenotype and said additional polymorphic locus; and
   (ii) detecting by genotyping said polymorphic locus that is linked with an ultra-firm watermelon flesh phenotype in at least one watermelon plant from said population of watermelon plants.

6. The method of claim 5, wherein the fruit of said selected watermelon plant comprising an introgressed locus linked with an ultra-firm watermelon flesh phenotype has flesh that resists a pressure of at least about 3.5 lb/F.

7. The method of claim 5, wherein cut flesh from the fruit of said selected watermelon plant loses less than about four percent water after three days storage at 4° centigrade.

8. The method of claim 5, wherein the polymorphic nucleic acid is located in a genomic region flanked by:
   a) loci NW0248953 (SEQ ID NO: 2) and NW0250718 (SEQ ID NO: 16);
   b) loci NW0248953 (SEQ ID NO: 2) and NW0251011 (SEQ ID NO: 12);
   c) loci NW0248953 (SEQ ID NO: 2) and NW0252274 (SEQ ID NO: 10);
   d) loci NW0250301 (SEQ ID NO: 3) and NW0250718 (SEQ ID NO: 16);
   e) loci NW0250301 (SEQ ID NO: 3) and NW0251011 (SEQ ID NO: 12); or
   f) loci NW0250301 (SEQ ID NO: 3) and NW0252274 (SEQ ID NO: 10).

9. The method of claim 5, wherein the introgressed locus linked with an ultra-firm watermelon flesh phenotype comprises at least one polymorphic nucleic acid that is linked with an ultra-firm watermelon flesh phenotype selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), and NW0250718 (SEQ ID NO: 16).

10. The method of claim 5, wherein the introgressed locus linked with an ultra-firm watermelon flesh phenotype comprises a genotype having at least one of: at least one allele of the C allelic state of the polymorphic nucleic acid of NW0252274 (SEQ ID NO: 10); at least one allele of the C allelic state of the polymorphic nucleic acid of NW0248646 (SEQ ID NO: 5); or at least one allele of the G allelic state of the polymorphic nucleic acid of NW0250301 (SEQ ID NO: 3).

11. A method of introgressing an allele into a watermelon plant, the method comprising:
(i) providing a population of watermelon plants;
(ii) genotyping at least one watermelon plant in the population with respect to a molecular marker located within 10 cM of at least one polymorphic nucleic acid selected from the group consisting of NW0250301 (SEQ ID NO: 3), NW0248646 (SEQ ID NO:5), and NW0252274 (SEQ ID NO:10),
(iii) selecting from the population at least one watermelon plant comprising said at least one polymorphic nucleic acid linked with an ultra-firm watermelon flesh phenotype; and
(iv) crossing said selected at least one watermelon plant to produce progeny comprising said at least one polymorphic nucleic acid linked with an ultra-firm watermelon flesh phenotype.

12. The method of claim 11, wherein the fruit of the selected watermelon plant has flesh that resists a pressure of at least about 3.5 lb/F.

13. The method of claim 11, wherein cut flesh of the fruit of the selected watermelon plant loses less than about four percent water after three days storage at 4° centigrade.

14. The method of claim 11, wherein the polymorphic nucleic acid is located in a genomic region flanked by:
a) loci NW0248953 (SEQ ID NO: 2) and NW0250718 (SEQ ID NO: 16);
b) loci NW0248953 (SEQ ID NO: 2) and NW0251011 (SEQ ID NO: 12);
c) loci NW0248953 (SEQ ID NO: 2) and NW0252274 (SEQ ID NO: 10);
d) loci NW0250301 (SEQ ID NO: 3) and NW0250718 (SEQ ID NO: 16);
e) loci NW0250301 (SEQ ID NO: 3) and NW0251011 (SEQ ID NO: 12); or
f) loci NW0250301 (SEQ ID NO: 3) and NW0252274 (SEQ ID NO: 10).

15. The method of claim 11, wherein at least one of said polymorphic nucleic acid is selected from the group consisting of NW0248953 (SEQ ID NO: 2), NW0250301 (SEQ ID NO: 3), NW0248949 (SEQ ID NO: 4), NW0248646 (SEQ ID NO: 5), NW0249077 (SEQ ID NO: 6), NW0249132 (SEQ ID NO: 7), NW0252494 (SEQ ID NO: 8), NW0248163 (SEQ ID NO: 9), NW0252274 (SEQ ID NO: 10), NW0248905 (SEQ ID NO: 11), NW0251011 (SEQ ID NO: 12), NW0248869 (SEQ ID NO: 13), NW0251470 (SEQ ID NO: 14), NW0251308 (SEQ ID NO: 15), and NW0250718 (SEQ ID NO: 16).

\* \* \* \* \*